(12) United States Patent
Rubin

(10) Patent No.: US 12,232,523 B2
(45) Date of Patent: Feb. 25, 2025

(54) FLAVOR ELEMENTS AND METHODS OF PROVIDING NONVAPORIZED FLAVOR TO ELECTRONIC VAPORIZERS AND E-CIGARETTES

(71) Applicant: Darren Rubin, Largo, FL (US)

(72) Inventor: Darren Rubin, Largo, FL (US)

(73) Assignee: Darren Rubin, Largo, FL (US)

( * ) Notice: Subject to any disclaimer, the term of this patent is extended or adjusted under 35 U.S.C. 154(b) by 0 days.

(21) Appl. No.: 18/301,804

(22) Filed: Apr. 17, 2023

(65) Prior Publication Data

US 2023/0248058 A1 Aug. 10, 2023

Related U.S. Application Data

(62) Division of application No. 16/709,555, filed on Dec. 10, 2019, now Pat. No. 11,632,985.

(51) Int. Cl.
*A24F 40/30* (2020.01)
*A23G 3/34* (2006.01)
(Continued)

(52) U.S. Cl.
CPC ............... *A24F 40/30* (2020.01); *A23G 3/34* (2013.01); *A24B 15/167* (2016.11); *A24F 40/20* (2020.01);
(Continued)

(58) Field of Classification Search
CPC ........ A24F 40/20; A24F 40/30; A24B 15/167; A23G 3/34; A61K 31/05; A61K 31/352; A61K 36/185
See application file for complete search history.

(56) References Cited

U.S. PATENT DOCUMENTS

2015/0208729 A1  7/2015  Monsees et al.
2016/0157520 A1  6/2016  Alfawaz et al.
(Continued)

FOREIGN PATENT DOCUMENTS

EP        3275319 A1 *  1/2018  ............. A24F 13/00

OTHER PUBLICATIONS

"Best JUUL Compatible Pods for CBD and Nicotine", Online article, retrieved from https://vaping360.com/best-vape-cartridges/juul-compatible-pods/ on Jan. 29, 2020.
(Continued)

*Primary Examiner* — Christopher M Rodd
*Assistant Examiner* — Ronnie Kirby Jordan
(74) *Attorney, Agent, or Firm* — Alston & Bird LLP

(57) ABSTRACT

The present disclosure describes a flavor element configured for providing flavor to a user of an electronic vaporizer, along with nicotine reduction methods. The flavor element includes a flavor material configured to provide the flavor and is configured to attach to the electronic vaporizer. When attached to the electronic vaporizer and during inhalation by the user using the electronic vaporizer, the flavor element is configured to provide the flavor to the user in parallel with an inhalable aerosol provided by the electronic vaporizer. The inhalable aerosol is provided by the electronic vaporizer by at least partially vaporizing a vaporizable substance via a vapor element. The flavor provided via the flavor material is separate from the vaporizable substance.

35 Claims, 22 Drawing Sheets

(51) Int. Cl.
- *A24B 15/167* (2020.01)
- *A24F 40/20* (2020.01)
- *A61K 31/05* (2006.01)
- *A61K 31/352* (2006.01)
- *A61K 36/185* (2006.01)

(52) U.S. Cl.
CPC ............ *A61K 31/05* (2013.01); *A61K 31/352* (2013.01); *A61K 36/185* (2013.01)

(56) References Cited

U.S. PATENT DOCUMENTS

| | | |
|---|---|---|
| 2016/0331036 A1 | 11/2016 | Cameron |
| 2016/0374398 A1 | 12/2016 | Amir |
| 2017/0035115 A1 | 2/2017 | Monsees et al. |
| 2018/0070647 A1 | 3/2018 | Monsees et al. |
| 2018/0199618 A1 | 7/2018 | Fuisz et al. |
| 2018/0352866 A1 | 12/2018 | Tucker et al. |
| 2019/0110519 A1 | 4/2019 | Meyer et al. |
| 2019/0116876 A1 | 4/2019 | Mankikian |
| 2019/0274354 A1 | 9/2019 | Sur et al. |
| 2019/0281891 A1 | 9/2019 | Hejazi et al. |

OTHER PUBLICATIONS

"JUUL" Internet Post, retrieved from https://www.juul.com/shop/pods/virgina-tobacco-5-percent, Jan. 28, 2020, 6 pages.

"SEA" product page, retrieved from https://www.theseabrand.com on Jan. 29, 2020, 23 pages.

"Stick Prince" product page, retrieved from https://www.smoktech.com/kit/stick-prince Apr. 10, 2020, 15 pages.

Damian, "JUUL Alternatives: Looking for a "JUUL-Like" Vape? here are the Top 5 Options!" internet article, retrieved from https://thevape.guide/juul-alternatives/ on Dec. 20, 2018, 13 pages.

Harrison "A New Smoking Gadget Says It's Safe. Should You Trust It?" E-Magazine, Nov. 7, 2019, 5 pages, Wired.

International Preliminary Report on Patentability issued in International Application No. PCT/US2020/054578 mailed on Jun. 23, 2022, 12 pages.

International Search Report and Written Opinion received for International Application No. PCT/US2020/054578, mailed on Feb. 17, 2021, 20 pages.

Rodriguez, "Cigarettes Vs. Vaping: that's The "Wrong Comparison," Says Inhalation Researcher" Journal, Nov. 4, 2019, 4 pages, Kaiser Health News.

Taney, "Nicotine Free JUUL Compatible Pods" Blog, posted Aug. 8, 2019, retrieved from https://www.vapor4life.com/blog/nicotine-free-juul-compatible-pods/ 13 pages.

Valinsky, "A New, Non-Vaping, Non-Smoking Way to Get Nicotine Has Come to America" News Article, Oct. 4, 2019, CNN Business, 3 pages.

Zhang, "E-Cigs Are Going Tobacco-Free With Synthetic Nicotine" Newsletter, Jun. 27, 2016, Wired, 12 pages.

"Creating Something Better for the World's Smokers," PowerPoint Presentation, Imperial Brands, 17 pages, (Oct. 1, 2018).

* cited by examiner

FLAVOR ELEMENTS AND METHODS OF PROVIDING NONVAPORIZED FLAVOR TO ELECTRONIC VAPORIZERS AND E-CIGARETTES

CROSS-REFERENCE TO RELATED APPLICATIONS

This application claims priority to U.S. patent application Ser. No. 16/709,555 filed Dec. 10, 2019, entitled "FLAVOR ELEMENTS AND METHODS OF PROVIDING NONVAPORIZED FLAVOR TO ELECTRONIC VAPORIZERS AND E-CIGARETTES", which is incorporated by reference herein, in its entirety for all purposes.

BACKGROUND OF THE DISCLOSURE

Electronic vaporizers have grown in popularity, especially those that vaporize nicotine, such as e-cigarettes. However, these electronic vaporizers have also grown in popularity among youths. What was once envisioned as a smoking cessation device for adults and a safer alternative to smoking cigarettes; which burn tobacco and release harmful carcinogens; has become a vaping epidemic among adults and teenagers. Even those individuals who have never smoked cigarettes before are quickly becoming addicted to the high level of nicotine found in nicotine (salt) containing liquids used to refill vaporizer reservoir tanks or in the disposable liquid pods of e-cigarettes. It is believed that flavor is largely responsible for this vaping epidemic. Much of the nicotine (salt) containing liquids and pods are candy or fruit flavored, thereby masking the awareness that these are addictive nicotine products. In reaction to the vaping epidemic, the U.S. Food & Drug Administration (FDA) is planning to ban e-cigarette flavors other than the flavor of tobacco and menthol. However, such a flavor ban on e-cigarettes may prevent adults wanting to stop smoking cigarettes from transitioning to e-cigarettes, as flavors may provide an incentive for such a switch. In addition, e-cigarette users may transition back to cigarettes, or switch to flavored cigars or flavored cigarillos as a result of the flavor ban. Note that Congress enacted the Family Smoking Prevention and Tobacco Control Act in 2009, which bans cigarettes with flavors other than menthol or tobacco, and may one day do the same for e-cigarette flavors if the FDA does not ban those flavors first to reduce the vaping epidemic among youths.

SUMMARY OF THE DISCLOSURE

The present disclosure provides apparatuses, systems, devices, flavor elements, and methods for providing enhanced flavor to an electronic vaporizer and user when vaping that is independent from the liquid or substance being vaporized. In other words, the enhanced flavor provided by this disclosure is not vaporized by the vapor element of the electronic vaporizer or e-cigarette, which may reduce potential to form harmful vapors. The enhanced flavor is provided by one or more flavor elements that are not in contact with the vapor element (the electrical resistor or heater that vaporizes a vaporizable substance to form a condensation aerosol available for inhalation). The flavor element(s) are associated with the electronic vaporizer or e-cigarette while the flavor element(s) have at least some portion that comes in contact with the lips and or mouth of the user, including when vaping.

Some embodiments of the disclosure can provide flavor to the user by contacting the user's lips and or mouth, even when not inhaling or even when the vaporizer is turned off. This allows the user to experience flavor even when not vaping or between vapes. This is believed to reduce the dependency of vaping.

By providing nonvaporized flavor element(s) to the electronic vaporizer and user, especially of non-tobacco or non-menthol flavor, the disclosed methods can provide the candy, fruit, or mint flavor that vapers desire without vaporizing the flavor substance. The embodiments presented herein may prevent e-cigarette users from switching back to cigarettes or flavored cigars (e.g., combustible products). The embodiments presented herein may also help e-cigarette users reduce their nicotine intake, without necessarily reducing vaping. This can be done by helping e-cigarette users gradually vape products with lower and lower nicotine content, and possibly even eventually vape nicotine-free e-cigarette products.

The present disclosure also provides apparatuses, systems, devices, flavor elements, and methods for reducing nicotine addiction by gradually reducing the nicotine content in one or more vaporizable substances, solutions, or refills to e-cigarettes and electronic vaporizers; some methods of which utilize adding flavor and or increasing flavor while reducing nicotine content.

The apparatuses, systems, devices, flavor elements, and methods disclosed herein, have various embodiments that work with various types of electronic vaporizers and e-cigarettes, including vaporizers that vaporize liquids, and/or vaporizers that heat and vaporize plant material, including tobacco products. Moreover, the apparatuses, systems, devices, flavor elements, and methods may work with electronic vaporizers that vaporize hemp or marijuana plant material, or cannabinoid oils (e.g., cannabidiol [CBD] oil) or other liquids. Similar to helping to reduce nicotine addiction, the described embodiments may also help reduce cannabinoid (e.g., tetrahydrocannabinol [THC]) dependency. Some embodiments add flavor or even increase flavor with flavor elements while reducing nicotine or cannabinoid content. Further embodiments may include an active pharmaceutical ingredient or therapeutic or medicinal substance in the flavor element to help overcome nicotine addiction or cannabinoid dependency (or addiction), and may optionally include at least one excipient ingredient. For example, in some embodiments the flavor element (e.g., a fruit, mint, or candy flavor element) includes a smoking cessation medicine, such as an active ingredient that binds nicotine receptors (e.g., varenicline, bupropion, cytisine, etc.). Or, the flavor element may contain other natural or holistic ingredients, some which may be available as natural or herbal supplements. These examples are not meant to be limiting. The active pharmaceutical ingredient or therapeutic or medicinal substance in the flavor element may be absorbed orally or transmucosally (e.g., sublingually).

In some embodiments, the flavor element contains an at least one vitamin and/or at least one mineral. For example, the flavor element provides vitamin C (ascorbic acid) and zinc to the user, such as for dietary supplementation. Such a combination may strengthen the immune system to reduce cold virus or respiratory virus symptoms.

Since nicotine is an addictive stimulant, a perhaps less harmful or less addictive stimulant can be included in the flavor element, e.g., such as a xanthine like caffeine. Since CBD oil and other cannabinoids are believed to treat pain, an analgesic or anti-inflammatory active ingredient, e.g., such as ibuprofen, can be included in the flavor element.

Other non-steroidal anti-inflammatory drugs (NSAIDs) or analgesics can be additionally or alternatively included. Again, these examples are not meant to be limiting, and one or more various active pharmaceutical ingredients can be included among the different classes of drugs.

In some embodiments, the flavor element comprises nicotine, a nicotine analogue or derivative, a cannabinoid, and/or a cannabinoid analogue or derivative. In some embodiments, the nicotine, nicotine analogue or derivative, cannabinoid, or cannabinoid analogue or derivative in the flavor element may be absorbed orally or transmucosally (e.g., sublingually). These flavor element embodiments including nicotine and or cannabinoid can complement the nicotine or cannabinoid content found in a vaporizable substance, or be used in methods to help reduce or eliminate the nicotine or cannabinoid content contained in a vaporizable substance or in a series of refills of vaporizable substance.

In some embodiments, the flavor of the flavor element may be reduced or even eliminated. For example, the flavor element may be flavored as menthol, tobacco, tobacco smoke, hemp/marijuana, or hemp/marijuana smoke, and in a series of flavor elements, this flavor may be reduced or even eliminated. This may be useful in methods to reduce vaping. Therefore, in some embodiments, the flavor element does not contain flavor at all or is or becomes flavorless.

Additionally or alternatively, some embodiments have a series of flavor elements where one or more flavors in the series increase while one or more different flavors in the series decrease. Such embodiments may have a unique sensory or psychological effect in reducing addiction or dependency of nicotine or cannabinoid.

In this disclosure, e-cigarettes may include at least a subset of electronic vaporizers. An example electronic vaporizer may include a housing or body generally made out of plastic and or metal. The housing generally houses (e.g., holds, retains, includes, etc.) a power source, such as a battery or rechargeable battery, and often has a charging port. Some electronic vaporizers may derive their electrical energy from a fuel cell or even a micro-turbine. One may even envision solar powered electronic vaporizers or electronic vaporizers that recharge from inductive charging or with an inductive charging pad. The housing generally also houses a controller or circuit board that runs (e.g., operates, controls, etc.) the vaporizer. Some electronic vaporizers may have one or more lights and/or displays, such as LED lights, such as to indicate when the electronic vaporizer is turned on, to indicate power level of the battery or when the unit requires a recharge, to indicate vaporization in use, to indicate vaporization temperature or power settings, or any combination thereof. Some electronic vaporizers may have switches or buttons for operation. Electronic vaporizers also have one or more vapor elements, which are generally an electrical resistor or heater, that are configured to heat a vaporizable substance, without burning, to generate a vapor. This vapor then cools forming a condensation aerosol available for inhalation out the output end of the electronic vaporizer when the user inhales. Electronic vaporizers generally also have a holding element or reservoir for containing the vaporizable substance. Some electronic vaporizers are breath activated using airflow sensors or pressure sensors. The output end of the electronic vaporizer may have a mouthpiece for the user to place in the mouth between his or her lips.

In some examples, electronic vaporizers may vaporize liquid vaporizable substances (e.g., a nicotine salt solution, CBD oil solution, etc.), may vaporize/partially vaporize solid or dried plant material (e.g., crushed tobacco leaves, material from hemp/marijuana plants, etc.), or any combination thereof. The plant material may be placed on a screen or mesh that either heats directly, or a heater is downstream to send warm air over the plant material to vaporize its more volatile attributes. The plant material is removed once used. This typically involves cleaning the electronic vaporizer. In some examples, an electronic vaporizer may be configured to receive a cartridge or disposable cartridge containing plant material, in addition to or alternative to the container being part of the electronic vaporizer.

One type of electronic vaporizer appears like a cigarette warmer. While not believed to accept standard cigarettes, these warming devices accept a modified cigarette, rather a cigarette-like stick (or heat stick) that contains dried tobacco leaves and other ingredients, such as propylene glycol and glycerin, which help form an aerosol. The electronic vaporizer is pen-shaped and contains a battery and heating element (vapor element). The cigarette-like stick inserts into the proximal end of the device and it is the cigarette-like stick that the user inhales from. Supposedly, these products have less toxins than standard cigarettes, especially since there is no combustion; no burning of the tobacco to generate carcinogenic tar. These devices need to be cleaned when the used cigarette-like stick is removed after use.

Liquid electronic vaporizers by far are the most popular, and comprise the bulk of the e-cigarette market. These come in two basic designs, vaporizers with refillable liquid tanks and e-cigarettes with prefilled, disposable liquid pods. Disposable liquid pods typically have a mouthpiece end incorporated with the pod. A primary difference among these vaporizers is that vaporizers with a refillable liquid tank generally have a reusable vapor element, or at least a vapor element that can outlast several tank refills. In contrast, electronic vaporizers with prefilled, disposable liquid pods contain a (disposable) vapor element within the disposable pod. There may be a wick or other element that aids fluid communication with the tank or pod and vapor element. Nicotine salt solutions (e.g., nicotine benzoate) for vaporization typically have a lower, more neutral pH than free base nicotine found in cigarettes, and thus, are often more pleasant even at these higher amounts.

Now comes the issue with flavor. Cigarette-like stick warmers are not believed to be allowed to have additional flavor other than its tobacco or menthol flavor. In contrast, liquid nicotine salt solutions can have a myriad of different flavors, from mint, to bubblegum, to cotton candy, to mango and other fruit flavors; which make these products much more palatable and desirable, if not addictive. But these additional flavors contained in the nicotine salt solution are vaporized alongside the nicotine salt itself, and some of these flavoring compounds themselves, or compounds formed during their vaporization, may cause irritation and toxicity as an aerosol. So while cigarette-like stick warming products, a supposedly better alternative to smoking cigarettes, may not be allowed to have flavored tobacco, the vaporized flavors of liquid nicotine solutions may be harmful. The present disclosure solves these problems. The present disclosure provides methods of providing nonvaporized flavor element(s) for electronic vaporizers, thereby providing additional flavors to cigarette-like stick warming products, and providing safe flavors to e-cigarette liquid vaporizers. Embodiments described herein may reduce the number of cigarette smokers in the US, which is now around 34 million Americans, and/or may help them to switch to better smokeless alternatives, and to eventually get them to quit smoking and vaping altogether, or at least reduce their dependency on nicotine. Because e-cigarette prefilled nicotine liquid pods containing flavors, such as bubble gum and cotton candy, have enticed numerous youths to smoke these vapor products, the FDA has proposed banning these candy flavored liquid pods, not least because there may be potential for these flavors, when vaporized, to cause irritation or toxicity themselves. However, the banning of such candy flavored nicotine pods can be of detriment to adult smokers looking to quit smoking cigarettes, which burn and release harmful secondhand smoke, and switch to safer vaporizer alternatives, such as e-cigarettes. An important part of the allure of e-cigarettes is that they need not taste like plain tobacco, and instead can have a myriad of fruit and candy flavors. Some manufacturers have even stopped selling certain flavors of nicotine solutions for vaporization.

The present disclosure provides apparatuses, systems, devices, flavor elements, and methods for making e-cigarettes flavorful again, such as for adult smokers, if flavored nicotine solutions were to be banned. Further, embodiments of the present disclosure provide safe, nontoxic, nonvaporized flavors for electronic vaporizers.

Embodiments of the disclosure also provide apparatuses, systems, devices, flavor elements, and methods of reducing nicotine content sequentially in a series of nicotine solutions or refills, or in liquid filled pods; for example, each pod or subset of pods having less nicotine content than the previous pod or subset of pods. Likewise, the disclosure provides methods of increasing flavor (e.g., candy flavor) content in a series of nicotine solutions or refills, or in liquid filled pods; for example, each pod or subset of pods having more flavor (e.g., candy flavor) than the previous pod or subset of pods. Still further, the disclosure provides methods of reducing nicotine content sequentially in a series of pods, each pod or subset of pods having less nicotine content than the previous pod or subset of pods; while about simultaneously increasing the flavor (e.g., candy flavor) content in a series of pods, each pod or subset of pods having more flavor (e.g., candy flavor) than the previous pod or subset of pods. In some embodiments the flavor is added to the liquid solution of the pods. In other embodiments, a flavor element is added, preferably externally to the pod, either on the exterior surface, such as on the mouthpiece, or incorporated into its plastic; although some embodiments of flavor elements can be inserted into the mouthpiece or output end itself.

Therefore, embodiments of the present disclosure may also provide apparatuses, systems, devices, flavor elements, and methods of introducing nonvaporized flavor to a vaporizer. In other words, at least one flavor not coming from the liquid in the tank nor from the liquid in the pod to be vaporized; i.e., a flavor not coming from the vapor of a vaporizable substance; even when the nonvaporized flavor is similar, identical, or different from a vaporized flavor of the vaporizable substance. In some embodiments, the nonvaporized flavor is different from the vaporized flavor. In some embodiments, the nonvaporized flavor matches or is similar to the vaporized flavor. The at least one flavor not coming from the liquid in the tank nor from the liquid in the pod to be vaporized can be associated with the mouthpiece tip of the vaporizer so that at least one of the user's lips, tongue, or saliva is in contact with it to receive flavor that can be transferred to the user's taste buds. The nonvaporized flavor can be associated with the mouthpiece tip of the vaporizer as a flavor element; for example as an at least one coating, sheath, gel, film, tape, elastomeric band, or mouthpiece extension or adaptor. This at least one flavor element may be comprised in a solid hard candy or gummy structure, or may be comprised in a syrup, gel, or powder coating. This at least one flavor element may be assembled with the mouthpiece during manufacture, or this at least one flavor element may be assembled or added to the mouthpiece by the user. After being depleted, the at least one flavor element may be reapplied to the mouthpiece or the at least one flavor element replaced. This is also an opportunity for the user to switch to a different flavor element or add an additional flavor or flavor element.

In other embodiments, the at least one flavor not coming from the liquid in the tank or pod to be vaporized is imbibed on a paper or filter or fiber element at or near the mouthpiece as a volatile or aromatic substance or essential oil, whereby the flavor gradually gets carried by inhalation to the tongue's taste buds, but is not vaporized directly by the vapor element.

In some embodiments, at least one mouthpiece of the vaporizer can be dipped by the user into a flavor substance, such as into a flavored powder, liquid, syrup or gel, so that at least some of the flavor substance gets associated with the mouthpiece. This process can be repeated as needed to maintain desired flavor.

In some embodiments, the flavor element is a mouthpiece extension or adaptor that insertably fits with the original mouthpiece or screws onto the outlet of the original mouthpiece of the vaporizer.

In some embodiments, the flavor substance gets associated with the mouthpiece of the vaporizer while the vaporizer is being stored in a case, and in some embodiments, get replenished that way.

Still further, in some embodiments the flavor substance gets associated with the mouthpiece of the vaporizer while the vaporizer is being electrically charged, or inductively being charged, and may be in a case that provides recharging of both energy and flavor/mouthpiece flavor.

In some embodiments, the flavor substance and or flavor element is advanced as needed as it gets used up or depleted. For example, an oval or rectangular flavor pouch or flavor holder can adhere to one of the long faces of the vaporizer. The flavor pouch or flavor holder can either be squeezed at its distal end, or a notch can be advanced proximally to advance the flavor substance or flavor element forward. In one example, the flavor substance is a gel or syrup that can be advanced forward much like a tube of toothpaste or squeeze-pouch. In another example, the flavor substance or flavor element comprises a hard candy post (e.g., like a candy cane) that can be advanced forward toward the mouthpiece tip as it gets used up. When the hard candy is associated with or proximal to the vaporizer mouthpiece tip, the hard candy can turn the vaporizer into a lollypop. In some embodiments, this hard candy post is retractable, when not in use. In some embodiments, the flavor element is retractable.

Some may desire, or eventually desire, a non-tobacco flavored vaping liquid for use with embodiments of this disclosure.

These together with other objects of the present disclosure, along with the various features of novelty which characterize embodiments of the present disclosure, are pointed out with particularity in the claims annexed to and forming a part of this disclosure. For a better understanding of the embodiments of the present disclosure, their operating advantages and the specific objects attained by their uses, reference should be had to the accompanying drawings and descriptive matter in which there is illustrated preferred embodiments of the disclosure.

Additional objects and advantages of embodiments of the present disclosure will be set forth in part in the description which follows, and in part will be obvious from the description, or may be learned by practice of embodiments of the present disclosure. The objects and advantages of the invention will be realized and attained by means of the elements and combinations particularly pointed out in the appended claims.

It is to be understood that both the foregoing general description and the following detailed description are exemplary and explanatory only and are not restrictive of embodiments of the present disclosure, as claimed.

BRIEF DESCRIPTION OF THE DRAWINGS

Embodiments of the present disclosure will be better understood and objects other than those set forth above will become apparent when consideration is given to the following detailed description thereof. Such description makes reference to the annexed drawings wherein.

DETAILED DESCRIPTION

With reference now to the drawings, embodiments of flavor elements and methods of providing nonvaporized flavor to electronic vaporizers and e-cigarettes embodying the principles and concepts of the present disclosure will be described in the following flavor element embodiments.

Figure 1:
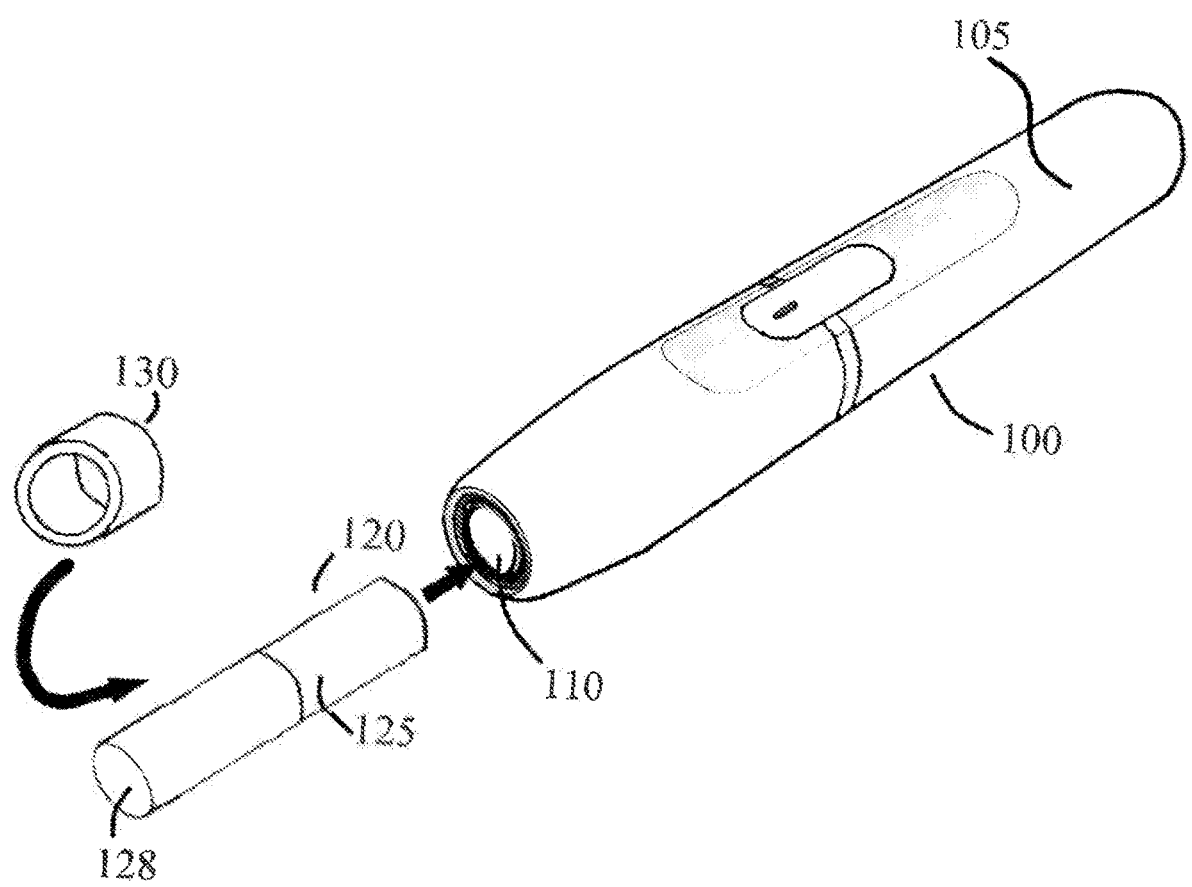
FIG. 1 is a perspective view of a first example flavor element configured for attachment to a heat stick of an example electronic vaporizer, in accordance with an embodiment of the present disclosure.
Figure 2:
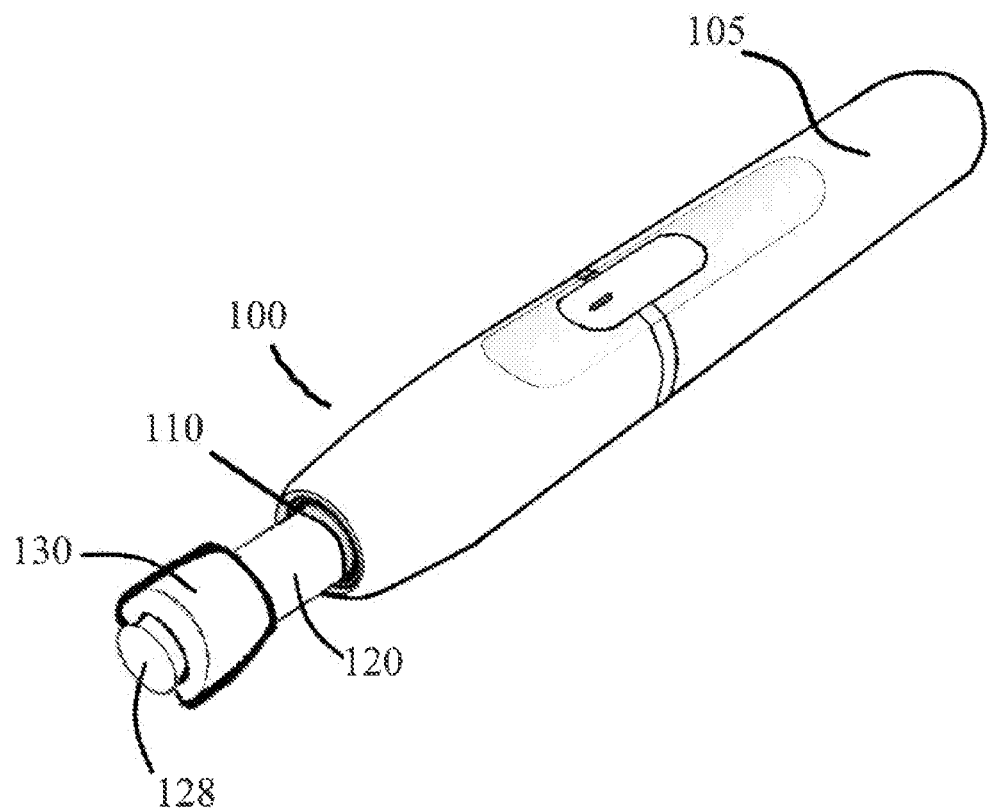
FIG. 2 is a perspective view of the flavor element of FIG. 1 attached to the heat stick of the example electronic vaporizer, in accordance with an embodiment of the present disclosure.

FIGS. 1 and 2 depict a first embodiment of a flavor element 130 in accordance with an embodiment of the disclosure. FIG. 1 is a perspective view of the flavor element 130 configured for attachment to a heat stick 120 of an example electronic vaporizer 100, in accordance with an embodiment of the present disclosure. FIG. 2 is a perspective view of the flavor element 130 of FIG. 1 attached to the heat stick 120 of the example electronic vaporizer 100, in accordance with an embodiment of the present disclosure.

The example electronic vaporizer 100 may include a tobacco stick warming, electronic vaporizer, in some examples. The example electronic vaporizer 100 may include a housing 105 with a proximal end 110, which includes heating elements (not shown) and an opening that is configured to accept (e.g., receive) a heat stick (e.g., rolled, cigarette-like, tobacco heat stick) 120 that includes a vaporizable substance. The heat stick 120 may include a paper or carbon fiber sheet 125 on the outside, and tobacco leaves (e.g., or some other plant-based) material 128 on the inside. The example electronic vaporizer 100 may be loaded the heat stick 120 at the proximal end 110. The heating elements may heat, without burning, materials of the heat stick 120.

The flavor element 130 may have a ring-like shape and may include a flavor material. In some examples, the flavor element 130 may include elastomeric or band-like flavor materials to form the ring-like shape, in some embodiments. In some examples, the elastomeric or band-like materials may include a licorice or gummy candy, and/or have adhesive along the inner side of the annular ring. The flavor element 130 may be configured to fit over, and/or adhere to, the heat stick 120, as indicated by the arrow.

As shown in FIG. 2, the example electronic vaporizer 100 is loaded with the heat stick 120, and the flavor element 130 of FIG. 1 is attached to the heat stick 120, and ready for use. When the user inhales, his or her lips are preferably placed onto, around, or over the flavor element 130, so that his or her mouth, saliva, and or tongue comes in contact with the flavor element 130 which imparts or releases flavor, and optionally, aroma, to the user that is, e.g., candy or fruit flavored. Wetting of the flavor element 130 by saliva may increase the amount of flavor released and or tasted. In some embodiments, the flavor element 130 is fully edible, for example, if comprising fully edible gummy candy, hard boiled candy (lollypop), taffy, or licorice. In some embodiments, the flavor element 130 is only partially edible, for example, the outer exterior may be edible, while leaving an inner non-edible material or plastic, e.g., a plastic ring, behind. For example, the flavor element 130 may comprise a plastic ring surrounded by an edible lollypop ring. In some embodiments, the flavor element 130 may include non-edible and contains flavor infused, embedded, and or coated onto its exterior. In some embodiments, it may be possible to place two or more of the flavor elements on the heat stick 120.

It is appreciated that the example electronic vaporizer 100 is exemplary, and that the flavor element 130 may be used with other electronic vaporizers having different sizes, shapes, arrangements, features, etc., without departing from the scope of the disclosure. The elements depicted in FIGS. 1 and 2 are exemplary and are not intended to be to scale. Accordingly, the relative sizes between the depicted elements may be different than depicted without departing from the scope of the disclosure.

Figure 3A:
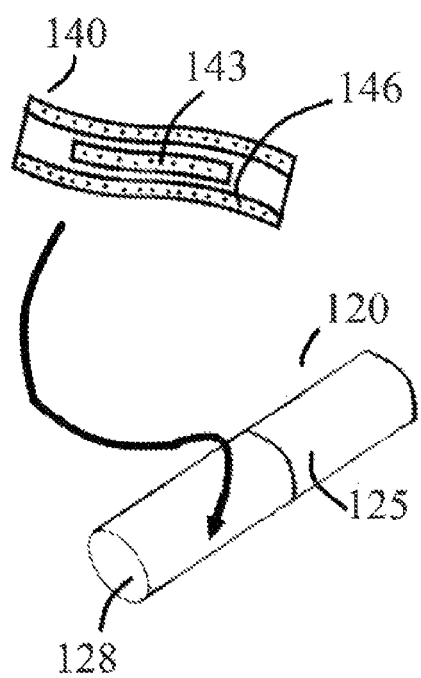
FIG. 3A is a perspective view of a second embodiment of a flavor element configured for attachment to a heat stick, in accordance with an embodiment of the present disclosure.
Figure 3B:
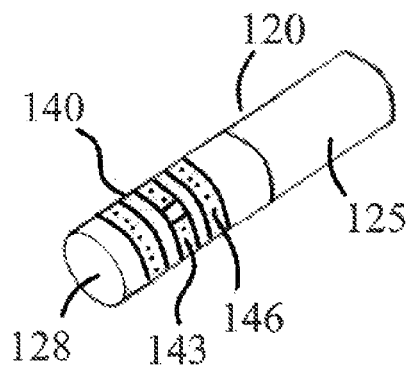
FIG. 3B is a perspective view of the flavor element of FIG. 3A attached to the heat stick, in accordance with an embodiment of the present disclosure.
Figure 4:
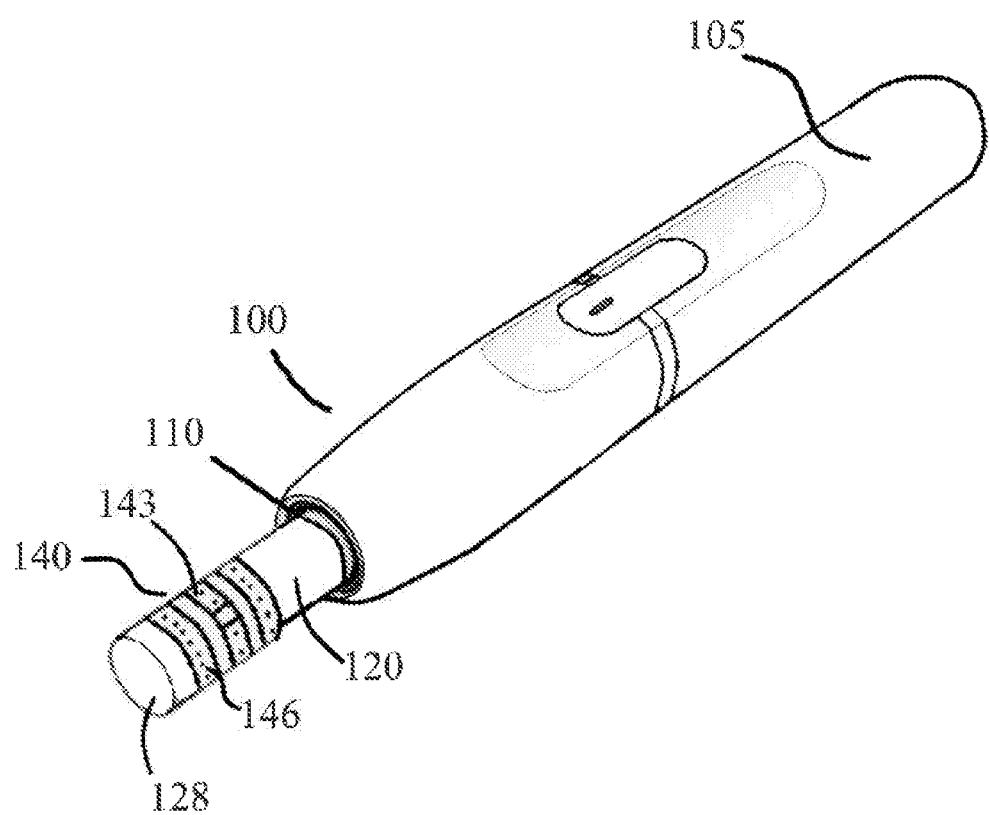
FIG. 4 is a perspective view of the flavor element of FIGS. 3A and 3B attached to the heat stick and installed in an example electronic vaporizer, in accordance with an embodiment of the present disclosure.

FIGS. 3A, 3B, and 4 depict a second embodiment of a flavor element 140 in accordance with an embodiment of the disclosure. FIG. 3A is a perspective view of the flavor element 140 configured for attachment to a heat stick 120, in accordance with an embodiment of the present disclosure. FIG. 3B is a perspective view of the flavor element 130 of FIG. 3A attached to the heat stick 120, in accordance with an embodiment of the present disclosure. FIG. 4 is a perspective view of the flavor element 130 of FIGS. 3A and 3B attached to the heat stick 120 and installed in an example electronic vaporizer 100, in accordance with an embodiment of the present disclosure. FIGS. 3A, 3B, and/or 4 may include elements that have been previously described with respect to FIGS. 1 and/or 2. Those elements have been identified in FIGS. 3A, 3B and/or 4 using the same reference numbers used in FIGS. 1 and/or 2 and operation of the common elements is as previously described. Consequently, a detailed description of the operation of these particular elements will not be repeated in the interest of brevity.

The flavor element 140 includes a flexible structure (e.g., a tape-like or film-like structure) made to wrap at least partially around a portion of the heat stick 120. In some embodiments, the flavor element 140 has one or more flavor materials on its top surface, and at least one adhesive on its bottom surface to adhere to the heat stick 120. In this example, the flavor element 140 has a first flavor area 143 with a first flavor material, and (optionally) a second flavor area 146 with a second flavor material. The respective flavor materials of the two flavor areas 143 and 146 may include different flavor materials, e.g., chocolate and banana flavors, or orange and cream flavors, in some examples. In other examples, the respective flavor materials of the two flavor areas 143 and 146 may include common flavor materials. These examples are not meant to be limiting, and there can be many thousands of different flavors and flavor combinations that can be implemented on the flavor element 140.

As shown in FIG. 3B, the flavor element 140 wrapped around, and/or adhered to, or associated with the heat stick 120. As shown in FIG. 4, the heat stick 120 with the flavor element 140 is loaded into the example electronic vaporizer 100, and is ready for use. When in use, the user's lips are preferably placed onto, around, or over the flavor element, so that his or her mouth, saliva, and or tongue comes in contact with the flavor element 140 which imparts or releases flavor, and optionally, aroma, to the user that is, e.g., candy or fruit flavored. Wetting of the flavor element 140 by saliva may increase the amount of flavor released and or tasted. In some embodiments, it may be possible to place a new flavor element 140 next to or over an existing flavor element 140 on the heat stick 120. In some embodiments, this flavor element 140 includes a film instead of or in addition to a tape. In some examples, the flavor element 140 may include a dissolvable film that dissolves over time after being wetted, such as by saliva. For example, the dissolvable film may be similar to the kind like Listerine® Cool Mint® breath strips; although in some embodiments, a slower dissolving may be desired. In some examples, the flavor element not only provides flavor during vaping, but further provides long-lasting breath freshening after vaping, e.g., such as to counter the aftertaste of tobacco/tobacco-flavored or *cannabis/cannabis*-flavored vaping.

It is appreciated that the example electronic vaporizer 100 is exemplary, and that the flavor element 140 may be used with other electronic vaporizers having different sizes, shapes, arrangements, features, etc., without departing from the scope of the disclosure. The elements depicted in FIGS. 3A, 3B, and 4 are exemplary and are not intended to be to scale. Accordingly, the relative sizes between the depicted elements may be different than depicted without departing from the scope of the disclosure.

Figure 5:
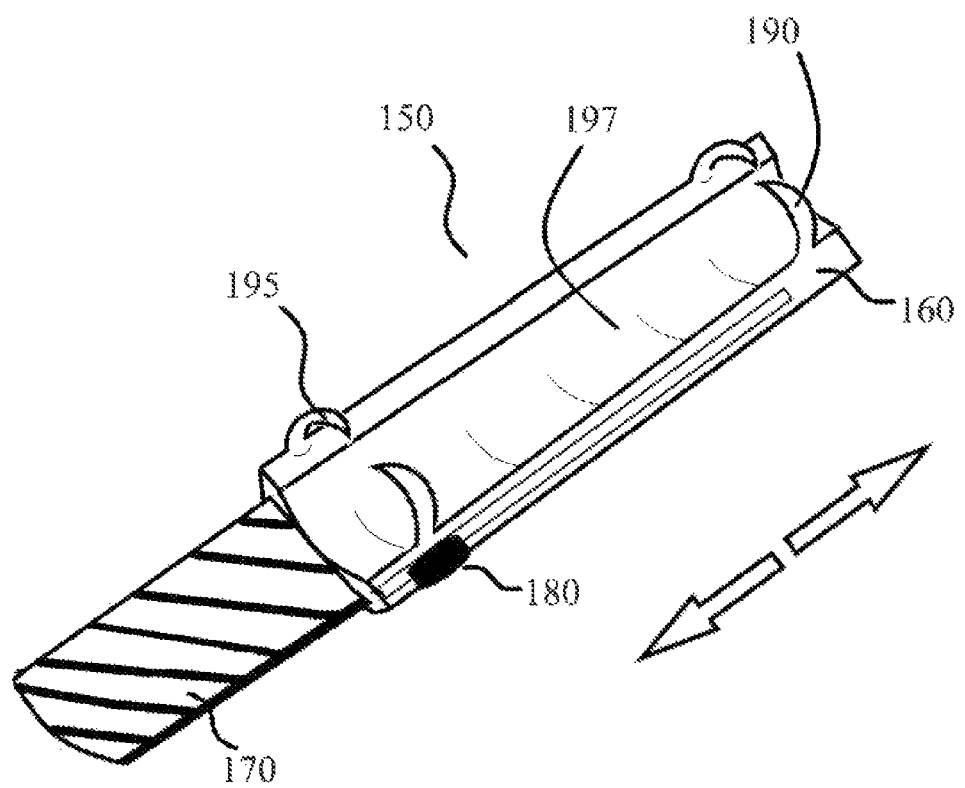
FIG. 5 is a perspective view of a third embodiment of a flavor element, in accordance with an embodiment of the present disclosure.
Figure 6A:
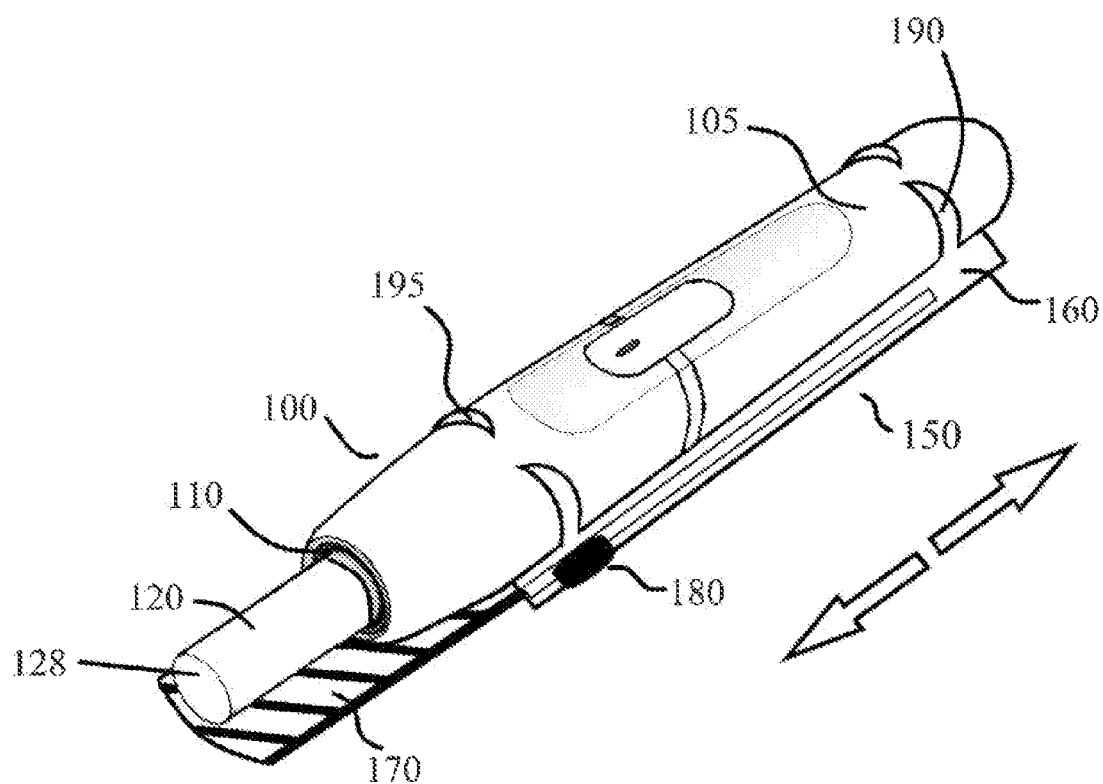
FIG. 6A is a perspective view of the flavor element of FIG. 5 installed on an example electronic vaporizer in a first configuration, in accordance with an embodiment of the present disclosure.
Figure 6B:
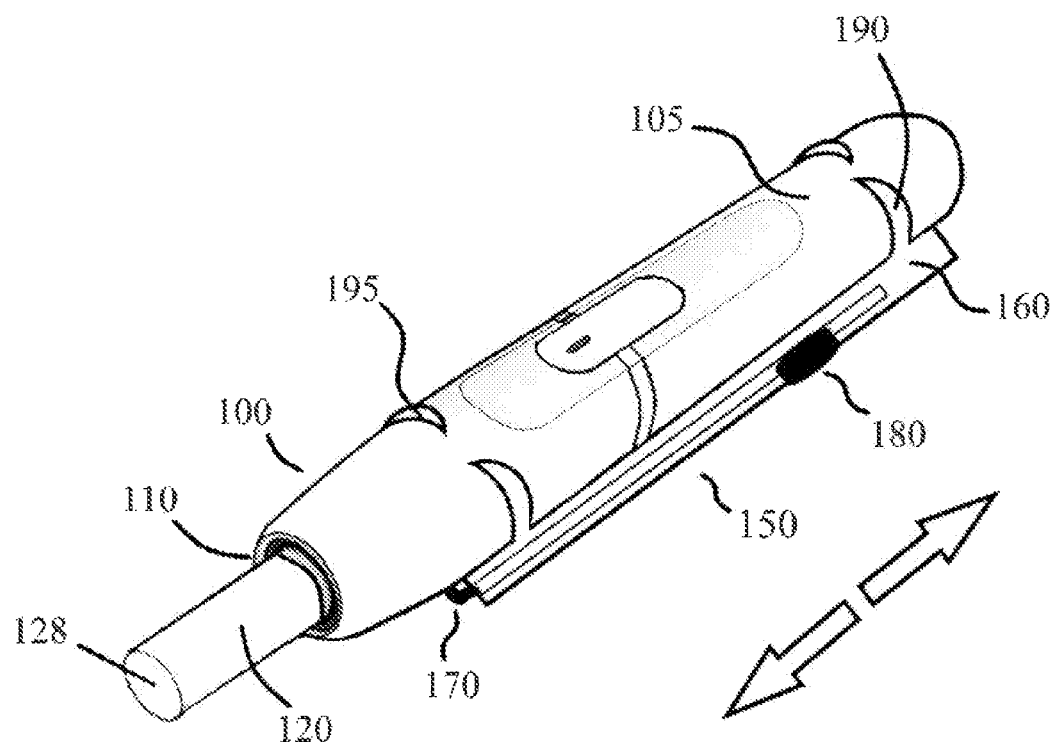
FIG. 6B is a perspective view of the flavor element of FIG. 5 installed on the example electronic vaporizer in a second configuration, in accordance with an embodiment of the present disclosure.

FIGS. 5, 6A, and 6B depict a third embodiment of a flavor element 150 in accordance with an embodiment of the disclosure. FIG. 5 is a perspective view of the flavor element 150, in accordance with an embodiment of the present disclosure. FIG. 6A is a perspective view of the flavor element 150 of FIG. 5 installed on an example electronic vaporizer 100 in a first configuration, in accordance with an embodiment of the present disclosure. FIG. 6B is a perspective view of the flavor element 150 of FIG. 5 installed on the example electronic vaporizer 100 in a second configuration, in accordance with an embodiment of the present disclosure. FIGS. 5, 6A, and/or 6B may include elements that have been previously described with respect to FIGS. 1 and/or 2. Those elements have been identified in FIGS. 5, 6A, and/or 6B using the same reference numbers used in FIGS. 1 and/or 2 and operation of the common elements is as previously described. Consequently, a detailed description of the operation of these particular elements will not be repeated in the interest of brevity.

As shown in FIG. 5, the flavor element 150 is a retractable/extendable, clip-on style flavor element that includes a mounting unit 160 and retractable post (e.g., a hard candy post or candy tongue depressor) 170 that includes a flavor material configured to provide a flavor. The retractable post 170 may be configured to retract or extend with a lever 180. The retractable post 170 may be comprised of a candy cane or other boiled candy or hard candy, such as a lollypop material or rock candy material. In some embodiments, the retractable post 170 may be less rigid, and may comprise a taffy or saltwater taffy candy. Clip mounts 190 and 195 may be included in some examples to attach the flavor element 150 to the example electronic vaporizer 100. In some examples, the clip mounts 190 and 195 may be included if an adhesive (not shown) is used to attach the flavor element 150 to the example electronic vaporizer 100. The double arrows show the direction that the lever 180 and the retractable post 170 each move. The flavor element 150 may be snapped onto, and or slid over, the example electronic vaporizer 100. However, the flavor element 150 can be arranged to attach to electronic vaporizers of various different shapes and sizes. As shown FIG. 6A, the retractable post 170 may be extended so as to be in proximity to the user's lips when using the example electronic vaporizer 100. In some embodiments, the user places his or her lips onto, around, and or over the retractable post 170 and the heat stick 120 simultaneously during inhalation to obtain non-vaporized flavor from the flavor element during vaping of the example electronic vaporizer 100. When the retractable post 170 is associated with or proximal to the example electronic vaporizer 100 mouthpiece tip, the hard candy can turn the example electronic vaporizer 100 into a lollypop. As the proximal end of retractable post 170 dissolves, becomes ingested, and or becomes depleted or used up, the lever 180 may be slid to further to extend the retractable post 170 to move remaining portions of the retractable post 170 in closer proximity to the user's mouth. Therefore, the flavor material of the retractable post 170 may include a candy post or strip that can be advanced forward toward the mouthpiece tip as it gets consumed. In some embodiments, the user tastes flavor from the flavor element 150 when not inhaling or between inhalations. In some embodiments, the flavor element 150 is retracted and the user does not taste flavor when not vaping. As shown in FIG. 6B, the retractable post 170 of the flavor element 150 is in a retracted position. The retractable post 170 may be retracted between vaping, or at times during vaping when flavor is not desired. In some embodiments, the flavor element 150 may include a non-ingestible material. When the retractable post 170 is about fully retracted, the mounting unit 160 may serve as a cover to protect the flavor material of the retractable post 170 from getting dirty before and/or between use.

It is appreciated that the example electronic vaporizer 100 is exemplary, and that the flavor element 150 may be used with other electronic vaporizers having different sizes, shapes, arrangements, features, etc., without departing from the scope of the disclosure. The elements depicted in FIGS. 5, 6A, and 6B are exemplary and are not intended to be to scale. Accordingly, the relative sizes between the depicted elements may be different than depicted without departing from the scope of the disclosure.

Figure 7A:
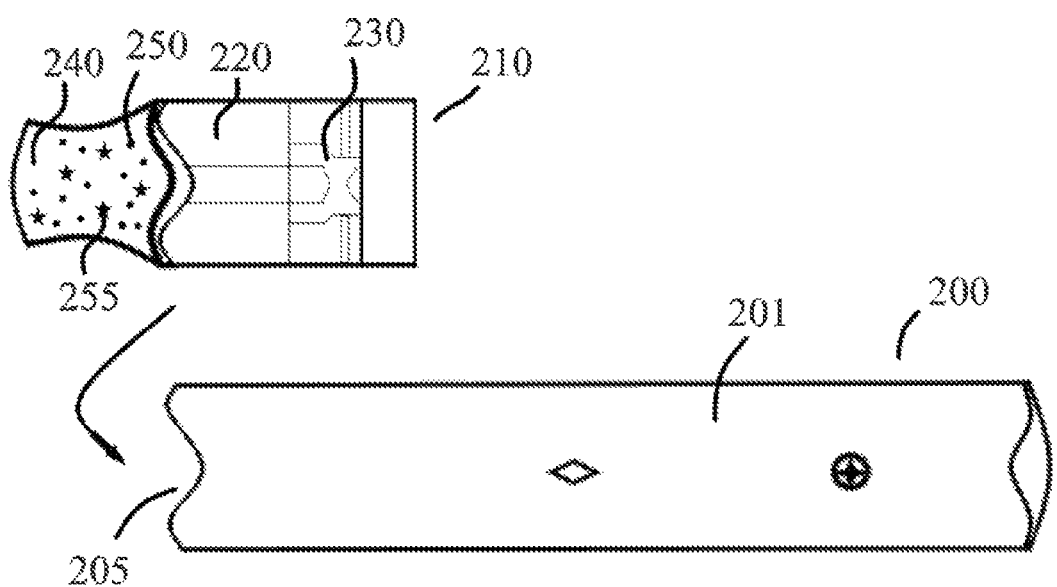
FIG. 7A is a perspective view of a fourth embodiment of a flavor element configured for installation on an example electronic vaporizer, in accordance with an embodiment of the present disclosure.
Figure 7B:
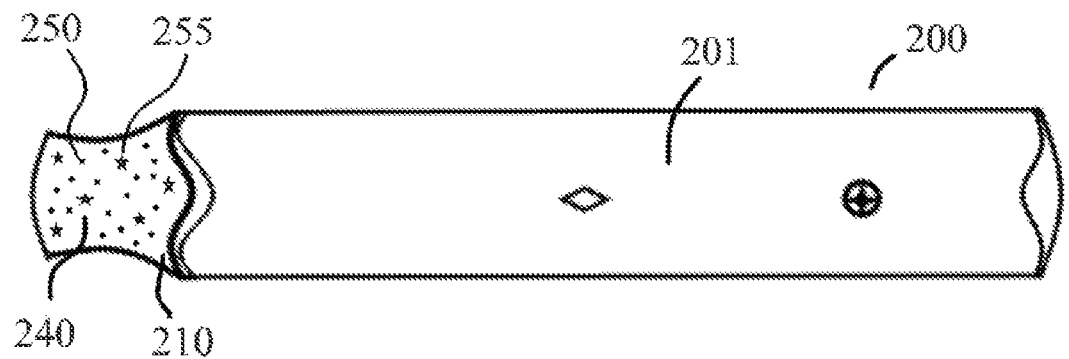
FIG. 7B is a perspective view of the flavor element of FIG. 7A installed on the example electronic vaporizer, in accordance with an embodiment of the present disclosure.

FIGS. 7A and 7B depict a fourth embodiment of a flavor element 250 in accordance with an embodiment of the disclosure. FIG. 7A is a perspective view of the flavor element 250 configured for installation on an example electronic vaporizer 200, in accordance with an embodiment of the present disclosure. FIG. 7B is a perspective view of the flavor element 250 of FIG. 7A installed on an example electronic vaporizer 200, in accordance with an embodiment of the present disclosure.

As shown in FIG. 7A the example electronic vaporizer 200 may include a housing 201 configured to receive a pod 210. In some examples, the pod 210 may be a vaporizable material 220. In some examples, the vaporizable material 220 may include a liquid, a gel, or any other type of fluid. In some examples, the pod 210 may be refillable. In some examples, the pod 210 may be single-use and/or disposable. The housing 201 of the example electronic vaporizer 200 has an opening or receptacle 205 at its proximal end to accept the pod 210. The vaporizable liquid 220 of the pod 210 may include a nicotine salt solution, in some examples, to be vaporized and aerosolized. Other types of materials may be included in the vaporizable material 220 without departing from the scope of the disclosure. The pod 210 also includes a heating element 230 inside and a mouthpiece end 240 contoured for engagement with a user's lips. As shown in, FIG. 7B, the pod 210 is loaded in the example electronic vaporizer 200 and is ready to use. The mouthpiece 240 may be detachable from the pod 210, and the portion of the pod 210 that contains the vaporizable material 220 and the heating element 230 may be a permanent part of the example electronic vaporizer 200.

The flavor element 250 including a flavor material 255 may be attached to the mouthpiece 240 of the pod 210. In some examples, the flavor element 250 includes one or more layers of the flavor material 255 that coats at least a portion of the mouthpiece 240. The one or more layers of the flavor material 255 of the flavor element 250 on the mouthpiece 240 may be applied by dipping the mouthpiece 240 into a source (e.g., pouch, package, bowl, bottle, tube, or any other container configured to hold the flavor material) (not shown) of the flavor material 255. In some embodiments, the mouthpiece 240 can be re-dipped or re-coated multiple times. In some embodiments, the flavor material 255 may include a powder, a gel, a syrup, a liquid, or any combination thereof.

In some embodiments, the flavor element 250 may include a sheath or sleeve that is configured to be placed over the mouthpiece 240. The sheath or sleeve may include a plastic-like wrap material, a nitrile glove-like material, a silicone material, an edible material, etc., or any combination thereof. In some examples, the sheath or sleeve may include the flavor material 255 (e.g., coated, infused, embedded, etc.) In some embodiments, the flavor element 250 may be part of the mouthpiece 240 or the pod 210.

It is appreciated that the example electronic vaporizer 200 is exemplary, and that the flavor element 250 may be used with other electronic vaporizers having different sizes, shapes, arrangements, features, etc., without departing from the scope of the disclosure. The elements depicted in FIGS. 7A and 7B are exemplary and are not intended to be to scale. Accordingly, the relative sizes between the depicted elements may be different than depicted without departing from the scope of the disclosure.

Figure 8A:
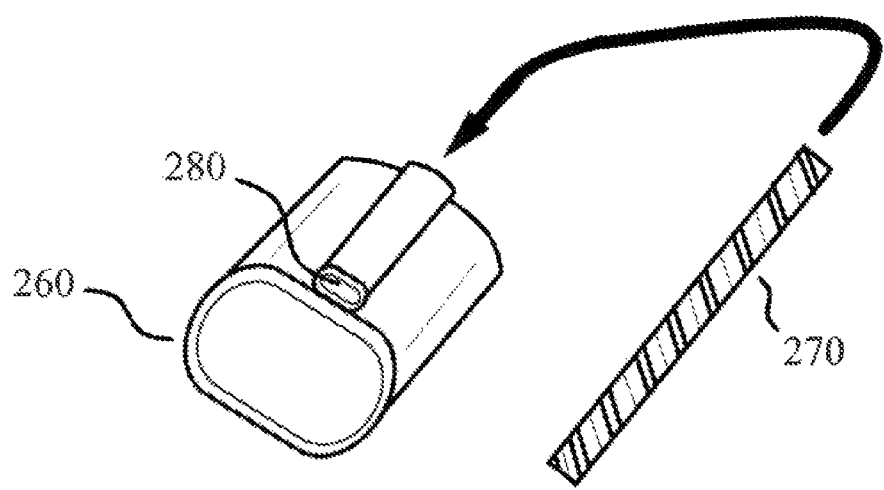
FIG. 8A is a perspective view of a fifth embodiment of a flavor element configured to receive an insert, in accordance with an embodiment of the present disclosure.
Figure 8B:
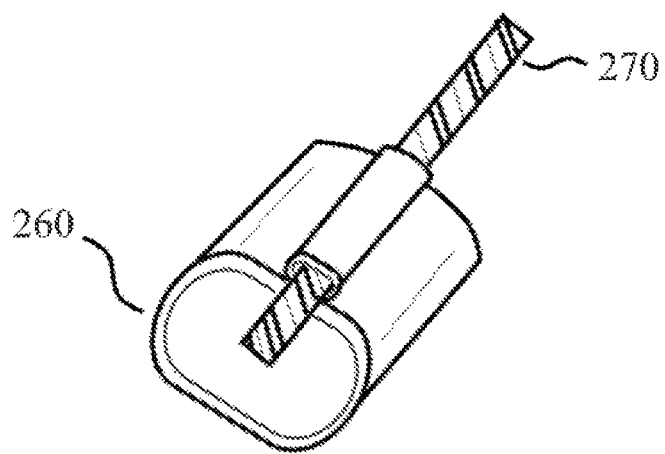
FIG. 8B is a perspective view of the flavor element of FIG. 8A with the insert installed, in accordance with an embodiment of the present disclosure.
Figure 9:
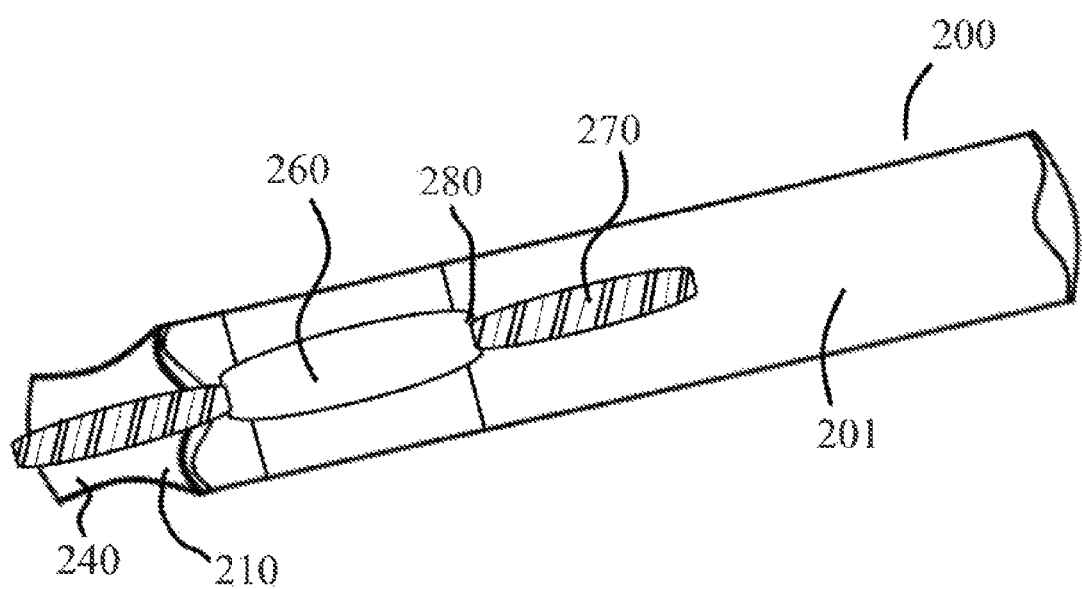
FIG. 9 is a perspective view of the flavor element of FIGS. 8A and 8B installed on an example electronic vaporizer, in accordance with an embodiment of the present disclosure.

FIGS. 8A, 8B, and 9 depict a fifth embodiment of a flavor element 260 in accordance with an embodiment of the disclosure. FIG. 8A is a perspective view of the flavor element 260 configured to receive an insert 270, in accordance with an embodiment of the present disclosure. FIG. 8B is a perspective view of the flavor element 260 of FIG. 8A with the insert 270 installed, in accordance with an embodiment of the present disclosure. FIG. 9 is a perspective view of the flavor element 260 of FIGS. 8A and 8B installed on an example electronic vaporizer 200, in accordance with an embodiment of the present disclosure. FIGS. 8A, 8B, and/or 9 may include elements that have been previously described with respect to FIGS. 7A and/or 7B. Those elements have been identified in FIGS. 8A, 8B, and/or 9 using the same reference numbers used in FIGS. 7A and 7B and operation of the common elements is as previously described. Consequently, a detailed description of the operation of these particular elements will not be repeated in the interest of brevity.

As shown in FIGS. 8A, 8B, and 9, the flavor element 260 may form a sleeve that is configured to fit over the part of the example electronic vaporizer 200, such as part of the housing 201, part of the mouthpiece 240, or any combination thereof. The insert 270 may be configured to slide into or out of a port 280 (e.g., an aperture extending longitudinally through a port structure attached to the sleeve), as shown by the arrow. The port 280 may have an ovular or circular shape, in some examples, although other shapes may be implemented without departing from the scope of the disclosure. The insert 270 may include a flavor material, such as a candy cane or licorice or. The insert 270 may include a lollypop or lollypop with stick that is configured to slide into the port 280, in some embodiments. As, shown in FIG. 8B, the insert 270 is loaded or slid into the port 280 of the flavor element 260. The flavor element 260 may have a tubular shape, in some embodiments. In some embodiments, the flavor element 260 may include an elastomeric material. In some embodiments, the flavor element 260 may be rigid or semi-rigid.

As shown in FIG. 9, the flavor element 260 with the insert 270 may be slid circumferentially over the example electronic vaporizer 200. The flavor element 260 may be installed on (e.g., attached to) the example electronic vaporizer 200 with the port 280 oriented on either on the top face, side face, or the bottom face of the example electronic vaporizer 200. In some examples, the bottom face may be preferred when wanting the insert 270 to directly touch the user's tongue.

In some embodiments, the flavor element 260 may include two or more of the ports 280, such as one on the top, bottom, and or sides of the example electronic vaporizer 200 (not shown). In some embodiments, the insert 270 can be advanced forward toward a tip of the mouthpiece 240 as it is consumed. When the insert 270 is associated with or proximal to the tip of the mouthpiece 240, the insert 270 effectively turn the example electronic vaporizer 200 into a lollypop.

It is appreciated that the example electronic vaporizer 200 is exemplary, and that the flavor element 260 may be used with other electronic vaporizers having different sizes, shapes, arrangements, features, etc., without departing from the scope of the disclosure. The elements depicted in FIGS. 8A, 8B, and 9 are exemplary and are not intended to be to scale. Accordingly, the relative sizes between the depicted elements may be different than depicted without departing from the scope of the disclosure.

Figure 10:
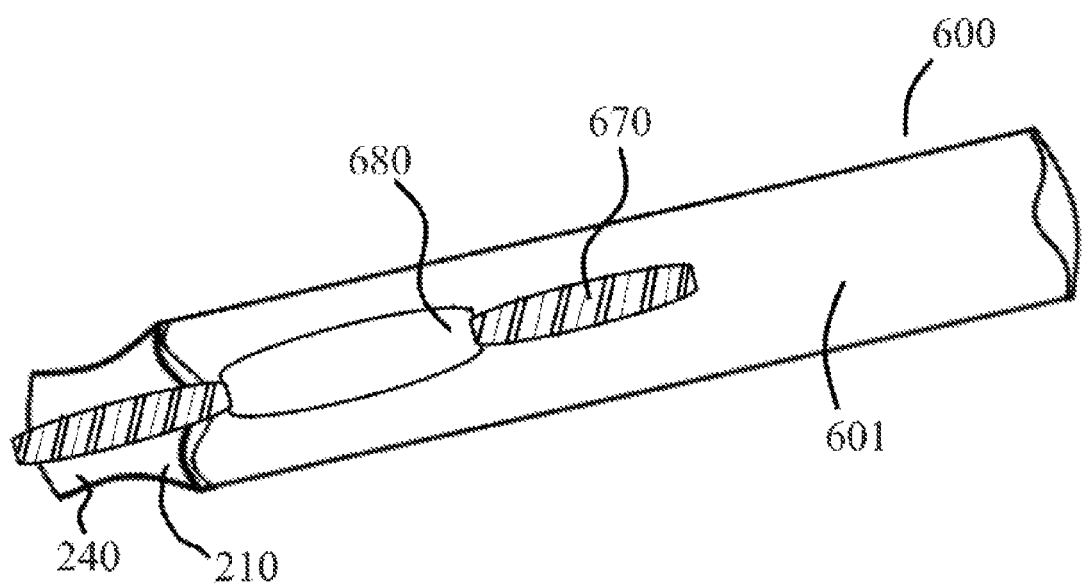
FIG. 10 depicts a sixth embodiment of a flavor element integrated with an example electronic vaporizer, in accordance with an embodiment of the present disclosure.

FIG. 10 depicts a sixth embodiment of a flavor element 670 integrated with an example electronic vaporizer 600, in accordance with an embodiment of the present disclosure. FIG. 10 may include elements that have been previously described with respect to FIGS. 7A, 7B, 8A, 8B, and/or 9. Those elements have been identified in FIG. 10 using the same reference numbers used in FIGS. 7A, 7B, 8A, 8B, and/or 9, and operation of the common elements is as previously described. Consequently, a detailed description of the operation of these particular elements will not be repeated in the interest of brevity.

As, shown in FIG. 10, the example electronic vaporizer 600 maybe similar to the example electronic vaporizer 200 of FIGS. 7A, 7B, and 9, except that a housing 601 includes a built-in or affixed flavor element structure 680 configured to receive the flavor element 670. The flavor element 670 may be slid or inserted into an aperture (e.g., ovular, circular, or any other shape) extending longitudinally through the flavor element structure 680, similar to the insertion of the insert 270 into the port 280, as described with reference to FIGS. 8A, 8B, and 9, except that the flavor element structure 680 is part of the example electronic vaporizer 600, rather than attached to a sleeve that can be readily installed or removed. As such, the flavor element structure 680 is an integral and/or structural component of the example electronic vaporizer 600, e.g., an integral and/or structural component of the housing 601. In some embodiments, the flavor element structure 680 may be fused and/or welded to the housing 601 during manufacture, or after manufacture of the housing 601. In some embodiments, the flavor element structure 680 may be molded with the housing 601 as a single unit during manufacture of the housing 601. In some embodiments, the flavor element structure 680 may be screwed into the housing 601 or otherwise permanently or semi-permanently mounted on or affixed to the housing 601.

The flavor element 670 may include a flavor material. In some examples, the flavor element 670 may be partially or fully edible. The flavor material of the flavor element 670 may include a hard or soft candy, a candy cane, licorice, a lollypop, a lollypop with stick, or any combination thereof. The flavor element 670 may include other materials without departing from the scope of the disclosure. The port 680 may be configured to accept various different types, shapes, and sizes of the flavor element 670, with various flavor materials. In some embodiments, the flavor element 670 may include a flavor film, a flavor tape, a powder or gel flavor material, or any combination thereof. Again, these examples are not meant to be limiting. In some embodiments, the flavor element 670 may be replaced after being depleted or depleted of the flavor material. In some embodiments, the flavor element 670 may be permanently attached or affixed to with the port structure 680 (not shown), with an ability to re-apply flavor material to the flavor element 670.

It is appreciated that the example electronic vaporizer 600 is exemplary, and that the flavor element 670 may be used with other electronic vaporizers having different sizes, shapes, arrangements, features, etc., without departing from the scope of the disclosure. The elements depicted in FIG. 10 are exemplary and are not intended to be to scale. Accordingly, the relative sizes between the depicted elements may be different than depicted without departing from the scope of the disclosure.

Figure 11A:
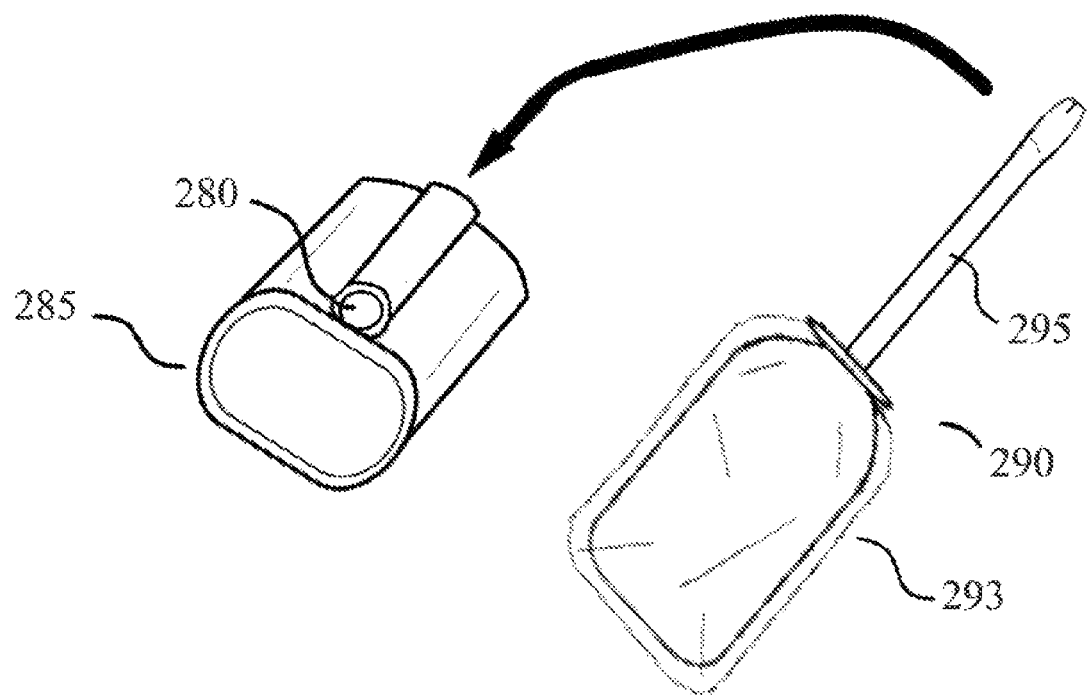
FIG. 11A is a perspective view of a seventh embodiment of a flavor element configured to receive an insert, in accordance with an embodiment of the present disclosure.
Figure 11B:
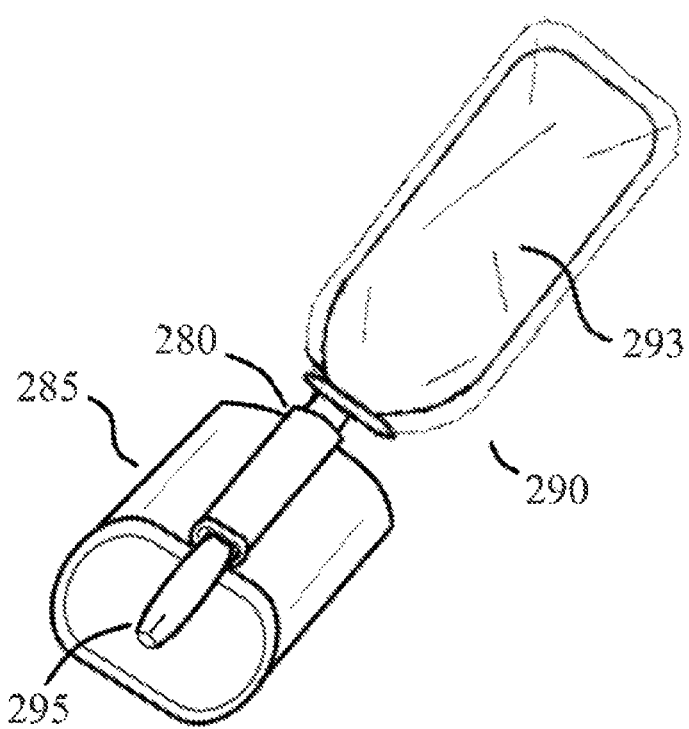
FIG. 11B is a perspective view of the flavor element of FIG. 11A with the insert installed, in accordance with an embodiment of the present disclosure.
Figure 12:
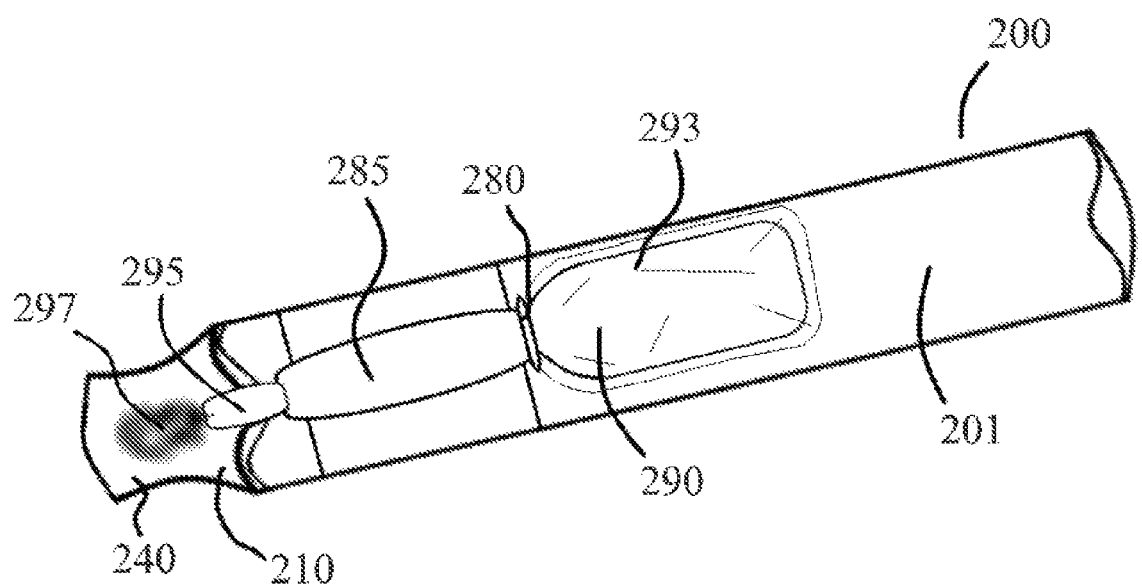
FIG. 12 is a perspective view of the flavor element of FIGS. 11A and 11B installed on an example electronic vaporizer, in accordance with an embodiment of the present disclosure.

FIGS. 11A, 11B, and 12 depict a seventh embodiment of a flavor element 285 in accordance with an embodiment of the disclosure. FIG. 11A is a perspective view of the flavor element 285 configured to receive an insert 290, in accordance with an embodiment of the present disclosure. FIG.

11B is a perspective view of the flavor element 285 of FIG. 11A with the insert 290 installed, in accordance with an embodiment of the present disclosure. FIG. 12 is a perspective view of the flavor element 285 of FIGS. 11A and 11B installed on an example electronic vaporizer 200, in accordance with an embodiment of the present disclosure. FIGS. 11A, 11B, and/or 12 may include elements that have been previously described with respect to FIGS. 7A, 7B, 8A, 8B, and/or 9. Those elements have been identified in FIGS. 11A, 11B, and/or 12 using the same reference numbers used in FIGS. 7A, 7B, 8A, 8B, and/or 9 and operation of the common elements is as previously described. Consequently, a detailed description of the operation of these particular elements will not be repeated in the interest of brevity.

As shown in FIGS. 11A and 11B, the flavor element 285 includes the port 280 configured to receive an insert 290. The insert 290 includes a tube 295 configured for insertion into the port 280, and a compressible container 293. The compressible container 293 may include flavor material. When the compressible container 293 is compressed or squeezed, a dose 297 of the flavor material from the compressible container 293 may be ejected from the insert 290 onto the mouthpiece 240 via the tube 295 when installed on the example electronic vaporizer 200. The dose 297 may provide flavor to the lips and or mouth of the user using the example electronic vaporizer 200. The flavor material included in the compressible container 293 may include a gel, a liquid, a powder, a paste, or any other type of material having fluid properties. As the flavor material included in the compressible container 293 is consumed, the compressible container 293 can be may be further compressed or squeezed some more to release more of the flavor material. The compressible container 293 may be configured to retain the flavor material (e.g., non-porous) and may have a flexible structure that allows for deformation when force is applied to the exterior. The compressible container 293 may be formed from a plastic material, a metallic material, an organic material, or any combination thereof. In some examples, the compressible container 293 may be formed from a material used to make juice pouches, squeezable yogurts tubes, toothpaste tubes, compressible bottles, or any combination thereof. In some examples, the compressible container 293 may be rolled at its end as flavor material is dispensed. In some embodiments, the tube 295 may be longer and/or may be positioned to be more proximal, so that the tube 295 ends right at, or goes inside, the user's mouth. In some examples, the flavor material may be consumed from the tube 295 by a sucking on or licking the tube 295, such as during vaping and or between vaping.

It is appreciated that the example electronic vaporizer 200 is exemplary, and that the flavor element 140 may be used with other electronic vaporizers having different sizes, shapes, arrangements, features, etc., without departing from the scope of the disclosure. The elements depicted in FIGS. 11A, 11B, and 12 are exemplary and are not intended to be to scale. Accordingly, the relative sizes between the depicted elements may be different than depicted without departing from the scope of the disclosure.

Figure 13:
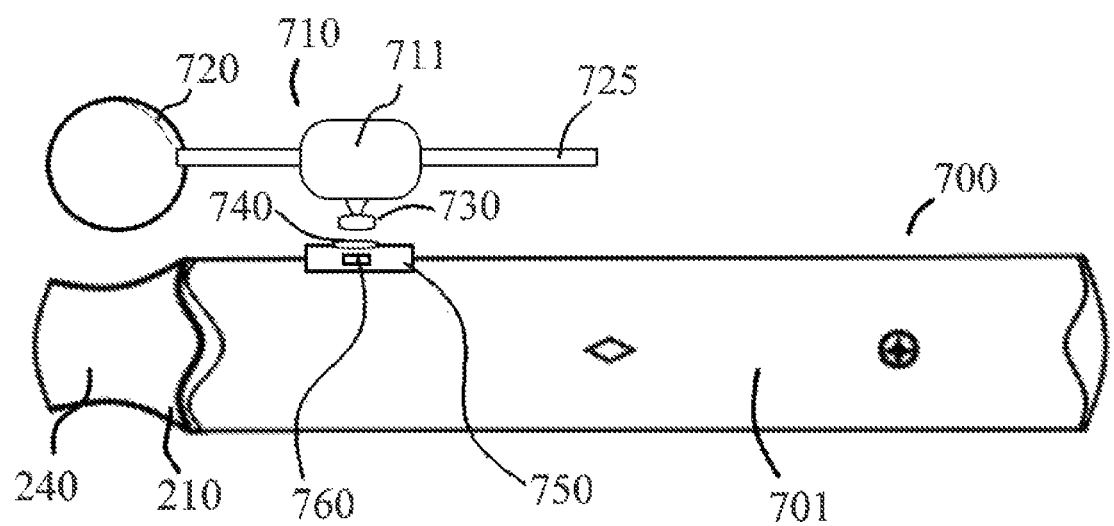
FIG. 13 depicts an eighth embodiment of a flavor element configured for installation on an example electronic vaporizer, in accordance with an embodiment of the present disclosure.

FIG. 13 depicts an eighth embodiment of a flavor element 710 configured for installation on an example electronic vaporizer 700, in accordance with an embodiment of the present disclosure. FIG. 13 may include elements that have been previously described with respect to FIGS. 7A, 7B, 8A, 8B, and/or 9. Those elements have been identified in FIG. 13 using the same reference numbers used in FIGS. 7A, 7B, 8A, 8B, and/or 9, and operation of the common elements is as previously described. Consequently, a detailed description of the operation of these particular elements will not be repeated in the interest of brevity.

As, shown in FIG. 13, the example electronic vaporizer 700 maybe similar to the example electronic vaporizer 200 of FIGS. 7A, 7B, and 9, except that a housing 701 includes a built-in or affixed flavor element structure 750 configured to receive the flavor element 710. The flavor element 710 may include a port structure 711 having an aperture extending longitudinally that is configured to receive an insert (e.g., flavor material 720 attached to a stick 725) and a connector 730 configured to mate with a connector 740 of the flavor element structure 750. The flavor element structure 750, in some embodiments, is an integral or structural component of the housing 701 (e.g., molded with the housing 701, fused or welded onto the housing 701, adhesively affixed to the housing 701, mechanically affixed using screws/bolts, etc., etc.).

In some embodiments, the flavor element structure 750 itself is removable or attachable. In the example shown, the connector 740 includes a female receptacle and the connector 730 includes a male extrusion or prong configured to mate with the female receptacle of the connector 740. It is appreciated that the connector 730 may include a female receptacle and the connector 740 may include a male extrusion or prong configured to mate with the female receptacle of the connector 730 without departing from the scope of the disclosure. In other examples, the connector 730 and the connector 740 may use other coupling mechanisms, such as slidable couplings, adhesive couplings, magnetic couplings, hardware couplings, hook and loop fastener couplings, etc. In some embodiments, the flavor element structure 750 has a release mechanism (e.g., switch, button, lever, etc.) 760 for coupling/decoupling and/or engagement/disengagement. Activating the release mechanism 760 allows the flavor element 710 to be removed from the flavor element structure 750. When the flavor element 710 is coupled to the example electronic vaporizer 700 via the flavor element structure 750, and is loaded the insert (e.g., the flavor material 720 attached to the stick 725), the flavor material 720 may be positioned to be near and/or adjacent to the mouthpiece 240 and/or the pod 210.

The insert depicted in FIG. 13 is exemplary, and many other types, shapes, sizes, etc. of the insert may be implemented or included without departing from the scope of the disclosure. In some embodiments, a magnetic coupling holds the flavor element structure 750 to the housing 701. In some embodiments, magnets or magnetic components hold the flavor element 710 directly onto the housing 701 (not shown). Again, these examples are not meant to be limiting; other means can be envisioned to couple the flavor element to the vaporizer, directly and or indirectly. In some embodiments, hook and loop fastener couplings can be used to hold the flavor element 710 to the flavor element structure 750. In some embodiments, hook and loop fastener couplings can be used to hold the flavor element structure 750 to the housing 701. In some embodiments, the flavor element 710 is held directly to the housing 701 by hook and loop fastener couplings (not shown).

It is appreciated that the example electronic vaporizer 700 is exemplary, and that the flavor element 710 may be used with other electronic vaporizers having different sizes, shapes, arrangements, features, etc., without departing from the scope of the disclosure. The elements depicted in FIG. 13 are exemplary and are not intended to be to scale. Accordingly, the relative sizes between the depicted elements may be different than depicted without departing from the scope of the disclosure.

Figure 14A:
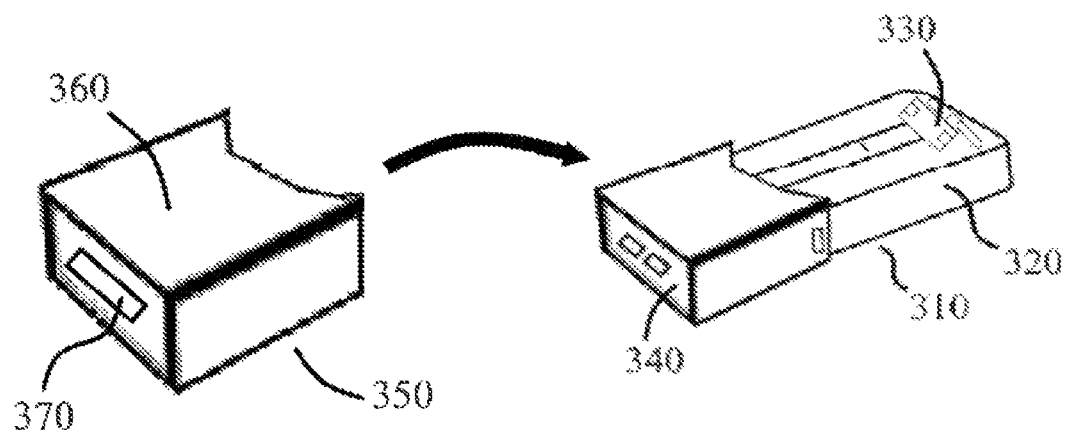
FIG. 14A is a perspective view of a ninth embodiment of a flavor element configured for attachment to a pod, in accordance with an embodiment of the present disclosure.
Figure 14B:
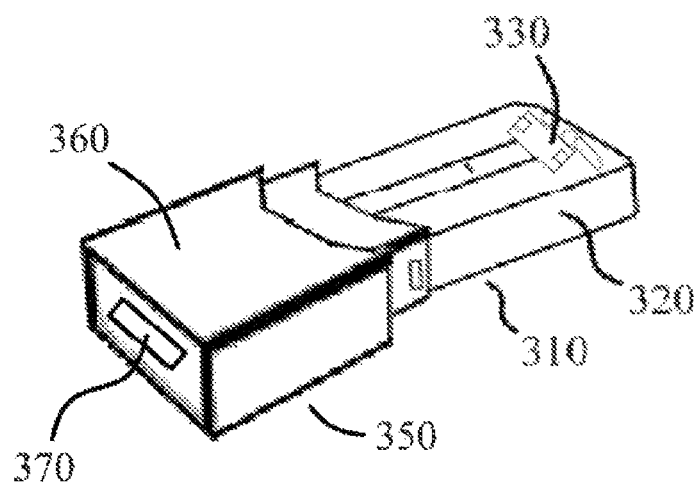
FIG. 14B is a perspective view of the flavor element of FIG. 14A attached to the pod, in accordance with an embodiment of the present disclosure.
Figure 14C:
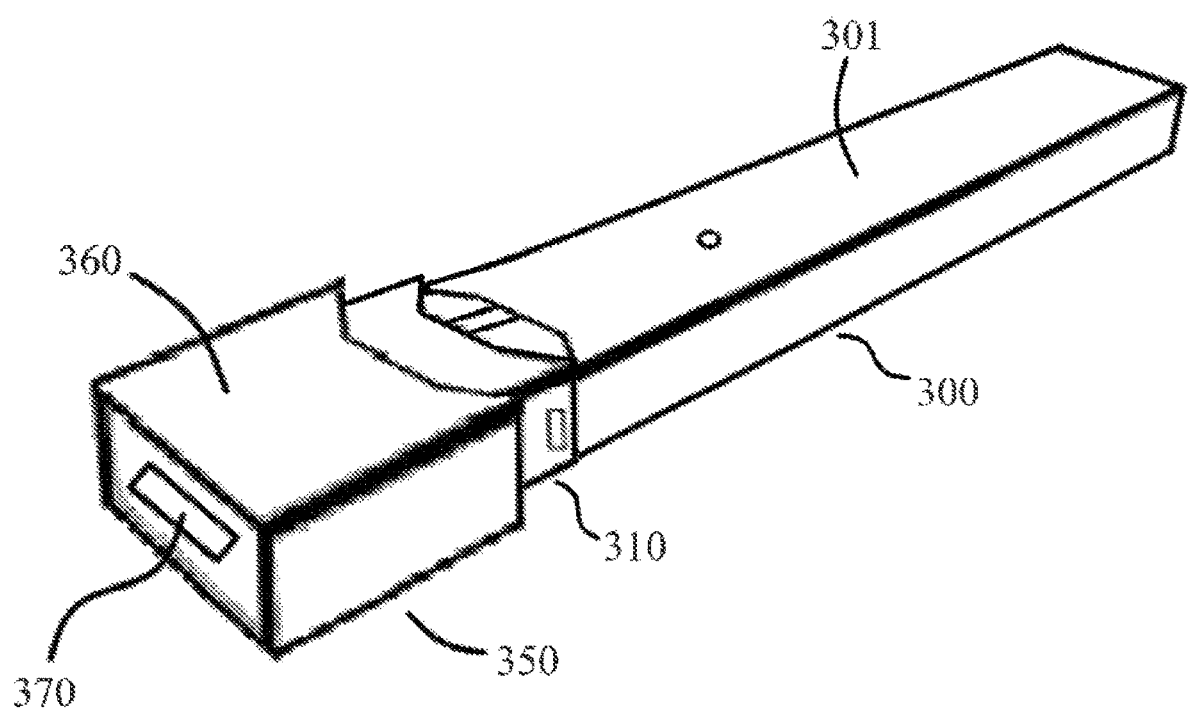
FIG. 14C is a perspective view of the flavor element of FIGS. 14A and 14B attached to the pod and installed in an example electronic vaporizer, in accordance with an embodiment of the present disclosure.

FIGS. 14A, 14B, and 14C depict a ninth embodiment of a flavor element 350 in accordance with an embodiment of the disclosure. FIG. 14A is a perspective view of the flavor element 350 configured for attachment to a pod 310, in accordance with an embodiment of the present disclosure. FIG. 14B is a perspective view of the flavor element 350 of FIG. 14A attached to the pod 310, in accordance with an embodiment of the present disclosure. FIG. 14C is a perspective view of the flavor element 350 of FIGS. 14A and 14B attached to the pod 310 and installed in an example electronic vaporizer 300, in accordance with an embodiment of the present disclosure.

The flavor element 350 may form a mouthpiece extension made to fit onto a mouthpiece end 340 of the pod 310. The pod 310 may include a vaporizable material 320 and a heating element 330. The example electronic vaporizer 300 has a housing 301 with an opening at its proximal end to accept the pod 310. The vaporizable material 320 in the pod 310 may include a liquid, gel, or other material with fluid properties. In some examples, the vaporizable material 320 may include a nicotine salt solution to be vaporized and aerosolized by the heating element 330. The mouthpiece end 340 may be configured for engagement with a user's lips. The flavor element 350 can have a flavor material embedded into its surface 360, or may include an edible material, such as a hard, boiled candy or hard flavored gelatin material. In some examples, the flavor element 350 can be a plastic or silicone material with flavor material embedded into its surface 360. In some embodiments, the flavor element 350 has one or more outlets 370 at its proximal end that are configured to align with one or more outlets of the mouthpiece end 340. The one or more outlets 370 may allow air and an inhalable aerosol (e.g., produced by heating the vaporizable material 320 via the heating element 330 when the example electronic vaporizer 300 is in use). The flavor element 350 can be assembled onto the pod 310 prior to installation of the pod 310 into the example electronic vaporizer 300 or after installation of the pod 310 into the example electronic vaporizer 300. The flavor element 350 may be configured to tightly form around the mouthpiece end 340 such that introduction of additional air inlets are avoided. This may prevent altering operation of an inhalation/pressure sensor of the example electronic vaporizer 300 (not shown).

Figure 14D:
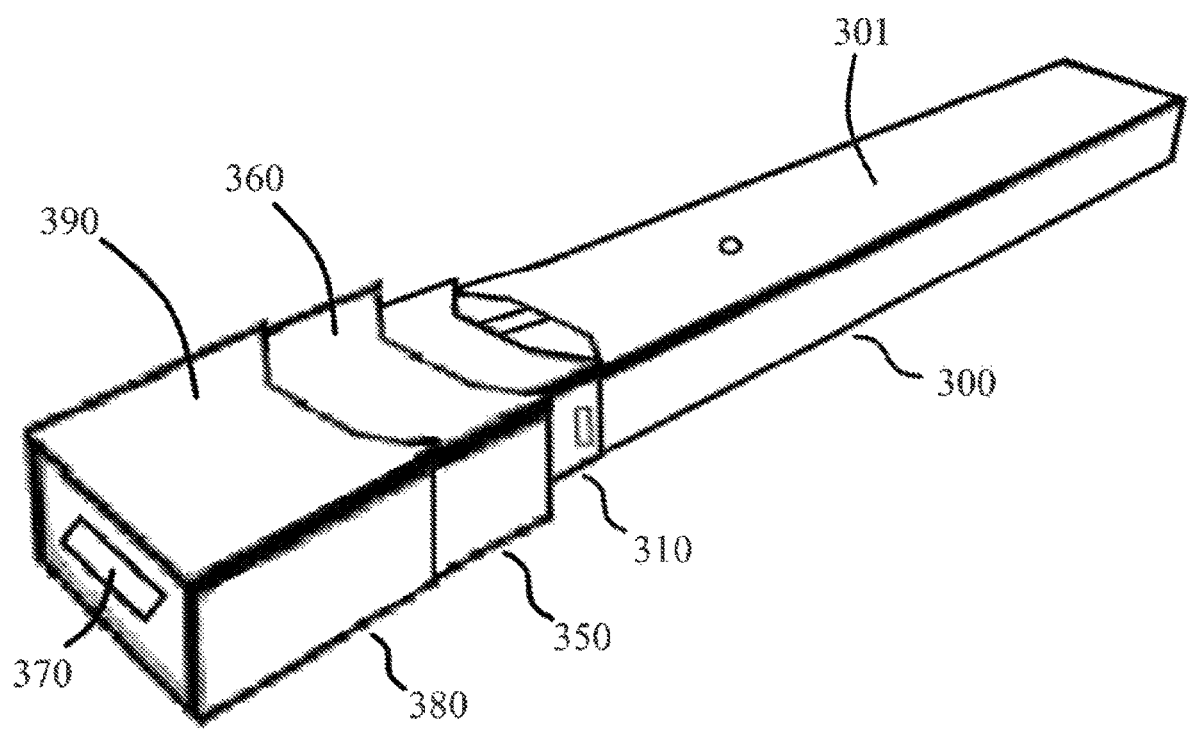
FIG. 14D is a perspective view of stacked flavor elements attached to a pod and installed in an example electronic vaporizer, in accordance with an embodiment of the present disclosure.

In some embodiments, two or more of the flavor elements 350 may be made to fit onto each other in a series, e.g., to stack them, such as to combine flavors or strengthen a flavor. FIG. 14D is a perspective view of stacked flavor elements 350 and 380 attached to the pod 310 and installed in the example electronic vaporizer 300, in accordance with an embodiment of the present disclosure. FIG. 14D may include elements that have been previously described with respect to FIGS. 14A, 14B, and/or 14C. Those elements have been identified in FIG. 14D using the same reference numbers used in FIGS. 14A, 14B, and/or 14C and operation of the common elements is as previously described. Consequently, a detailed description of the operation of these particular elements will not be repeated in the interest of brevity.

As shown in FIG. 14D, the flavor element 380 is stacked on the flavor element 350. The flavor element 380 may be constructed similar to the flavor element 350, except that it may be slightly larger than the flavor element 350 such that it is able to fit over the flavor element 350. The flavor element 380 can have a flavor material embedded into its surface 390, or may include an edible material, such as a hard, boiled candy or hard flavored gelatin material. In some examples, the flavor element 380 can be a plastic or silicone material with flavor material embedded into its surface 390. The flavor material of the flavor element 380 may include a different flavor material of the flavor element 350, in some examples. In some embodiments, if the flavor element 350 does not function like a mouthpiece to pass inhalable aerosol or air flow through it, and rather just fits onto the mouthpiece end 340 of the pod 310, then the flavor element 350 may just be considered a mouthpiece adapter or output end adapter.

It is appreciated that the example electronic vaporizer 300 is exemplary, and that the flavor elements 350 and 380 may be used with other electronic vaporizers having different sizes, shapes, arrangements, features, etc., without departing from the scope of the disclosure. The elements depicted in FIGS. 14A, 14B, 14C, and 14D are exemplary and are not intended to be to scale. Accordingly, the relative sizes between the depicted elements may be different than depicted without departing from the scope of the disclosure.

Figure 15A:
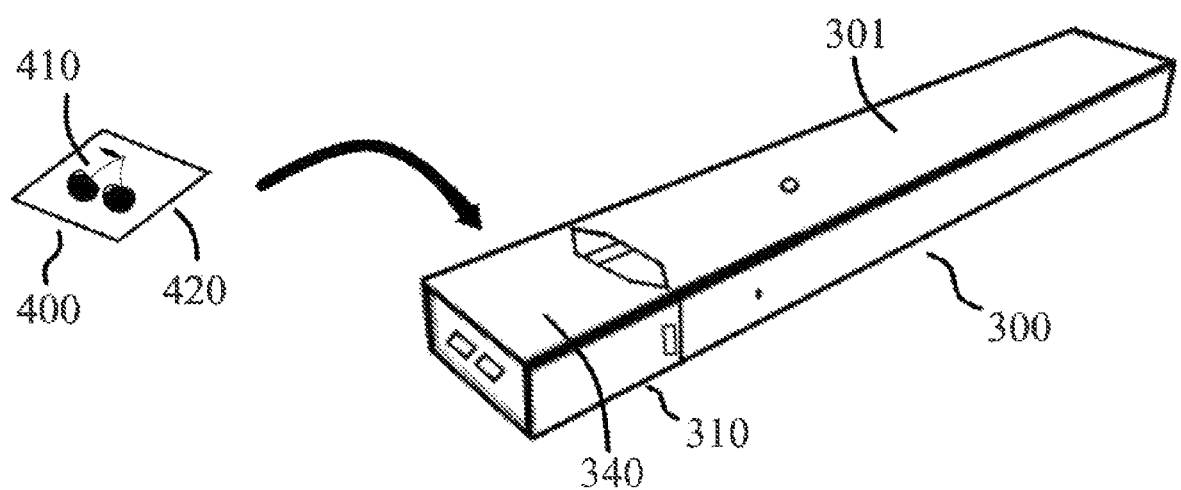
FIG. 15A is a perspective view of a tenth embodiment of a flavor element configured for installation on an example electronic vaporizer, in accordance with an embodiment of the present disclosure.
Figure 15B:
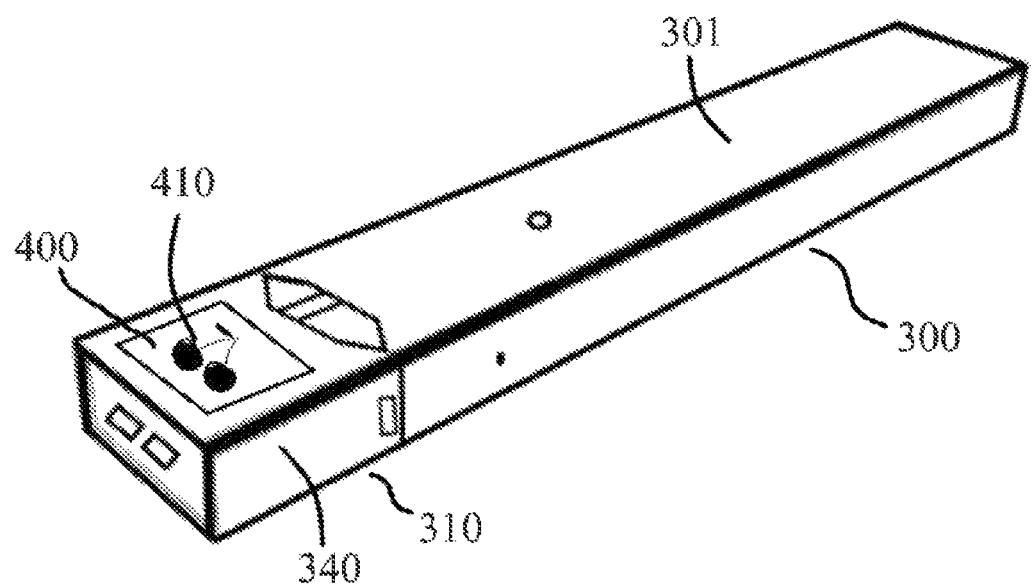
FIG. 15B is a perspective view of the flavor element of FIG. 15A when installed on the example electronic vaporizer, in accordance with an embodiment of the present disclosure.

FIGS. 15A and 15B depict a tenth embodiment of a flavor element 400 in accordance with an embodiment of the disclosure. FIG. 15A is a perspective view of the flavor element 400 configured for installation on an example electronic vaporizer 300, in accordance with an embodiment of the present disclosure. FIG. 15B is a perspective view of the flavor element 400 of FIG. 15A when installed on the example electronic vaporizer 300, in accordance with an embodiment of the present disclosure. FIGS. 15A and 15B may include elements that have been previously described with respect to FIGS. 14A, 14B, 14C, and/or 14D. Those elements have been identified in FIGS. 15A and 15B using the same reference numbers used in FIGS. 14A, 14B, 14C, and/or 14D and operation of the common elements is as previously described. Consequently, a detailed description of the operation of these particular elements will not be repeated in the interest of brevity.

The flavor element 400 may include a material that renders it be similar to a stamp or sticker with an adhesive or adhesive bottom layer 420 that can adhere to the mouthpiece end 340 of the pod 310. The top surface 410 of the flavor element 400 has a flavor material embedded in it. In some examples, the top layer 410 may also include an indication or description of the flavor of the flavor material (e.g., a drawing, a name, a word or words, etc.). In the specific example depicted in FIGS. 15A and 15B, the top surface 410 includes an indication that the flavor material includes a cherry flavor (e.g., based on a depiction of cherries drawn on the top surface 410). As shown by arrow, the flavor element 400 adheres on a surface of the mouthpiece end 340 of the pod 310. The flavor material of the top surface 410 may be exposed to the user's lips and or mouth and or saliva during use. In some embodiments, two or more of the flavor elements 400 can adhere to the housing 301 of the example electronic vaporizer 300 or to the pod 310 (e.g., multiple flavor elements 400 may be applied to common or different areas or faces of the mouthpiece end 340). In some embodiments, a new flavor element 400 can adhere on top of a used flavor element 400 to refresh or replenish the flavor. In some embodiments, a used and or depleted flavor element 400 is peeled off or removed and replaced with an undepleted or fresh flavor element 400.

It is appreciated that the example electronic vaporizer 300 is exemplary, and that the flavor element 400 may be used with other electronic vaporizers having different sizes, shapes, arrangements, features, etc., without departing from the scope of the disclosure. The elements depicted in FIGS. 15A and 15B are exemplary and are not intended to be to scale. Accordingly, the relative sizes between the depicted elements may be different than depicted without departing from the scope of the disclosure.

Figure 16A:
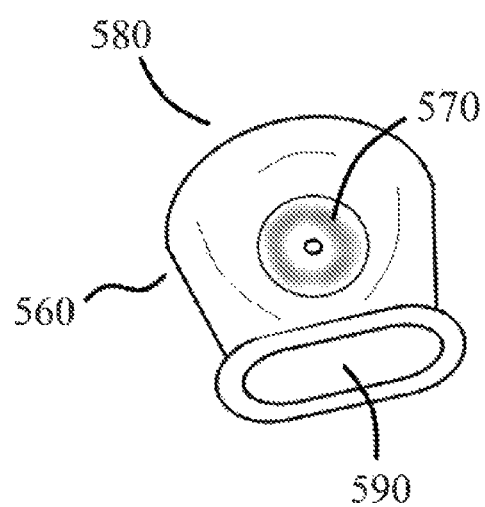
FIG. 16A is a perspective view of an eleventh embodiment of a flavor element, in accordance with an embodiment of the present disclosure.
Figure 16B:
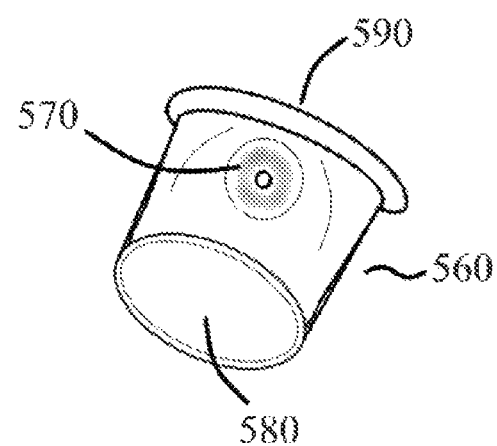
FIG. 16B is a second perspective view of the flavor element of FIG. 16A, in accordance with an embodiment of the present disclosure.
Figure 17:
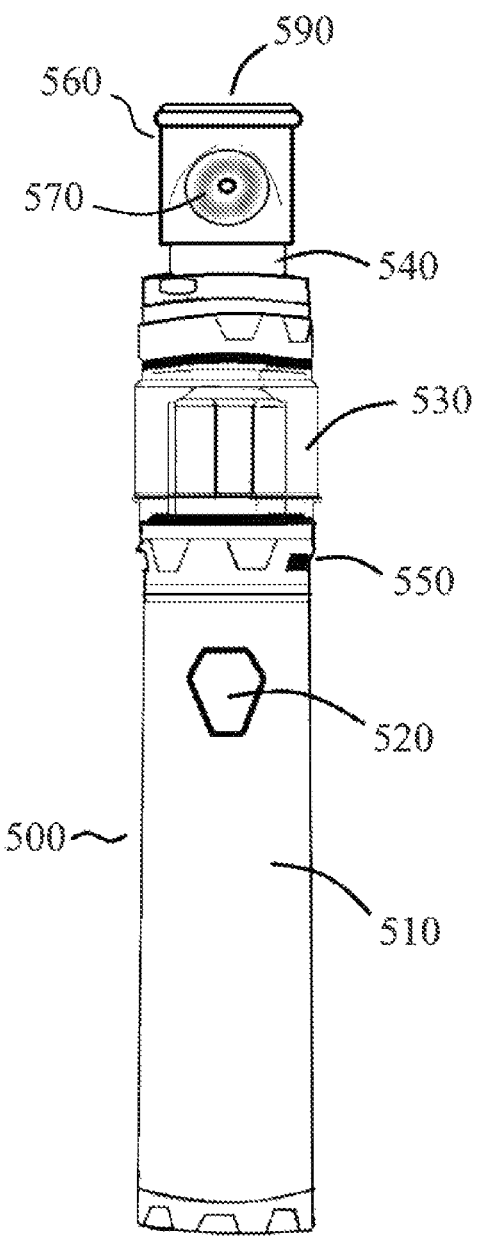
FIG. 17 is a perspective view of the flavor element of FIGS. 16A and 16B attached to a first example electronic vaporizer, in accordance with an embodiment of the present disclosure.

FIGS. 16A, 16B, and 17 depict an eleventh embodiment of a flavor element 560 in accordance with an embodiment of the disclosure. FIG. 16A is a first perspective view of the flavor element 560, in accordance with an embodiment of the present disclosure. FIG. 16B is a second perspective view of the flavor element 560 of FIG. 16A, in accordance with an embodiment of the present disclosure. FIG. 17 is a perspective view of the flavor element 560 of FIGS. 16A and 16B attached to an example electronic vaporizer 500, in accordance with an embodiment of the present disclosure.

The example electronic vaporizer 500 includes a housing 510 that contains a rechargeable battery and controller inside (not shown), a power button 520, reservoir 530 configured to hold a vaporizable substance, and an outlet end 540, and an airflow inlet vent 550. The reservoir 530 can hold vaporizable substances in the form of fluids, gels, powders, or any other material with fluid properties. In some examples, the vaporizable substance may include a nicotine salt solution, a cannabinoid solution, or any combination thereof. The reservoir 530 may also include a reusable vapor or heating element.

The flavor element 560 may serves as a mouthpiece or vapor outlet adapter for the example electronic vaporizer 500. The flavor element 560 includes a flavor section 570 that includes a flavor material. The shape or design of the flavor sections 570 depicted in FIGS. 16A, 16B, and 17 is exemplary, and it is appreciated that other shapes may be implemented without departing from the scope of the disclosure. In some embodiments the flavor section 570 is permanent and embedded in the flavor element 560. In some embodiments, the flavor section 570 is configured to have replaceable flavor material after some or all of the flavor material is consumed, or to accommodate changing to a different flavor material. In some examples, the flavor material may be in the form of a disc configured for insertion into the flavor sections 570. As such, the disc of flavor material can be removed from the flavor section 570 and replaced with another disc. In some embodiments, the flavor element 560 may include additional flavor sections 570, such as multiple flavor sections oriented around an outside surface of the flavor element 560. In some examples, the flavor element 560 can be removed from the example electronic vaporizer 500 and/or replaced with a different one of the flavor element 560.

In this example, the flavor element 560 includes a generally round input end 580 for accepting the output end of the example electronic vaporizer. Accordingly, the flavor element 560 has its own output end 590 that engages with the lips and or mouth of the user during use of the example electronic vaporizer 500. In some examples, the flavor element 560 may be formed from an elastomeric material to hold the flavor element 560 onto the output end 540 of the example electronic vaporizer 500. In some examples, a size of the input end 580 and/or a size of the output end 590 may be based on a size of the output end 540 of the example electronic vaporizer 500. The flavor element 560 can provide better contour engagement with the user's lips than the outlet end 540 of the example electronic vaporizer 500, in some examples.

In some embodiments, the flavor element 560 can engage with the lips and or mouth of the user even when vaporization is not taking place. In some examples, the flavor element can engage with the lips and or mouth of the user even when the flavor element 560 is not installed on with the example electronic vaporizer 500. The ability to provide flavor without vaporization of the example electronic vaporizer 500 with the flavor element 560 is a method may reduce an urge to vape, which may reduce dependency. Over time, the user may utilize the flavor element 560 more and more without vaporization taking place. Eventually, the user may be able to quit vaping with this method, or switch to nicotine-free or cannabinoid-free vaping solutions.

Figure 18:
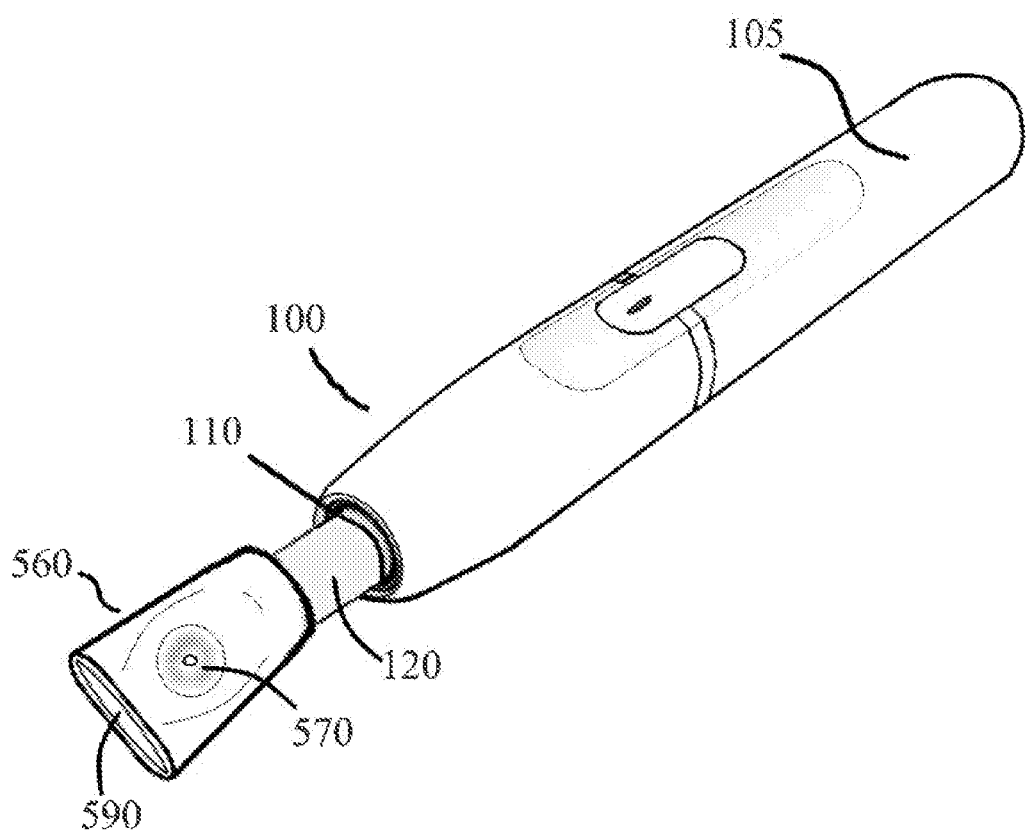
FIG. 18 is a perspective view of the flavor element of FIGS. 16A and 16B attached to a second example electronic vaporizer, in accordance with an embodiment of the present disclosure.

FIG. 18 is a perspective view of the flavor element 560 of FIGS. 16A and 16B attached to an example electronic vaporizer 100, in accordance with an embodiment of the present disclosure. FIG. 18 may include elements that have been previously described with respect to FIGS. 1, 2, 16A, 16B, and/or 17. Those elements have been identified in FIG. 18 using the same reference numbers used in FIGS. 1, 2, 16A, 16B, and/or 17 and operation of the common elements is as previously described. Consequently, a detailed description of the operation of these particular elements will not be repeated in the interest of brevity.

As shown in FIG. 18, the flavor element 560 may be installed on the heat stick 120 of the example electronic vaporizer 100. In some embodiments, a size of the input end 580 and/or a size of the output end 590 of the flavor element 560 may be narrower or smaller than the relative sizes of the flavor element 560 of FIG. 17. Furthermore, in some embodiments used with the heat stick 120, the flavor element 560 may at least partially comprise a hard material, e.g., plastic material; and in some embodiments, may at least partially comprise a paper or carbon fiber sheet material similar to a material used to construct the heat stick 120. In some embodiments, the flavor element 560 may be integrated with the heat stick 120 as a single unit (not shown).

It is appreciated that the example electronic vaporizers 100 and 500 are exemplary, and that the flavor element 560 may be used with other electronic vaporizers having different sizes, shapes, arrangements, features, etc., without departing from the scope of the disclosure. The elements depicted in FIGS. 16A, 16B, 17, and 18 are exemplary and are not intended to be to scale. Accordingly, the relative sizes between the depicted elements may be different than depicted without departing from the scope of the disclosure.

Any one or more of the various flavor element embodiments described herein (e.g., the flavor elements 130, 140, 150, 250, 260, 270, 670, 285, 710, 360, 390, 400, and 560 of FIGS. 1-18, respectively) may be used with various electronic vaporizers and e-cigarettes. The flavor elements shown are not limited for use with just the associated vaporizer type it is shown with. The examples of electronic vaporizers, e-cigarettes, and flavor elements shown are not meant to be limiting.

In some examples, any one or more of the various flavor element embodiments described herein may serve as aroma elements, thereby providing a pleasing scent to the user, such as to accompany the flavor and or enhance the flavor sensation. In some embodiments, an essential oil includes a portion of the flavor element to release aroma into the air near the user's nose and mouth.

Any one or more of the various flavor element embodiments described herein may include of one or more various substances, ingredients, active ingredients, excipients, solutions, and or formulations, and therefore, are not meant to be limiting.

Any one or more of the various flavor element embodiments described herein may provide sweet flavor, bitter flavor, sour flavor, mint flavor, tobacco flavor, menthol flavor, hemp flavor, fruit flavor, chocolate flavor, vanilla flavor, soda flavor, cola flavor, root beer flavor, liquor flavor, or any combination thereof, and are not meant to be limiting.

In some examples, any one or more of the various flavor element embodiments described herein may contain ethanol to provide some alcohol to the user. For example, any one or more of the various flavor element embodiments described herein may alcohol in a chocolate liquor flavor. In other examples, any one or more of the various flavor element embodiments described herein may provide a flavor of a spirits, such as wine, whiskey, bourbon, scotch, beer, vodka, rum, tequila, margarita, daiquiri, colada, or a combination thereof, and may optionally provide at least some ethanol to the user or be alcohol-free. By including some alcohol in the flavor, it may require identification, such as an adult driver's license, in order to purchase the flavor element, so that children cannot obtain it. Because alcohol is highly combustible, vaporizers cannot contain much alcohol in its vaporizable substance or liquid. Therefore, a nonvaporized flavor element containing alcohol is possible with lower risk of combustion.

In some embodiments, any one or more of the various flavor element embodiments described herein may have an effect on the tongue, such as providing a tingling sensation. In some embodiments, the flavor element provides some effervescence to the user, for example, providing Pop Rocks® effervescent candy, or similar candy containing pressurized carbon dioxide gas bubbles embedded inside.

In some embodiments, any one or more of the various flavor element embodiments described herein may be capable of being covered, e.g., such as to not become dirty when put down on a table or other surface. Therefore, any one or more of the various flavor element embodiments described herein may include at least one cover (not shown).

The disclosed flavor element embodiments for providing flavor to a user of an electronic vaporizer or e-cigarette. The flavor element embodiments may be associated with the electronic vaporizer when providing flavor to the user when the user places the electronic vaporizer to the user's lips and or mouth. The electronic vaporizer essentially comprises a housing, an energy source, a source of vaporizable substance, an output end, and a vapor element comprising an electrical resistor or heater. When in use, the electronic vaporizer provides an inhalable aerosol at the output end when the vaporizable substance is at least partially vaporized by the vapor element. The flavor element is noncontacting and unassociated with the vapor element of the electronic vaporizer, i.e., the flavor element does not come into contact with the vapor element of the electronic vaporizer. The flavor element is separate from, and or does not comprise, the vaporizable substance to be vaporized by the vapor element. Therefore, the flavor element or its flavor thereof does not get vaporized by the vapor element of the electronic vaporizer. Therefore, the flavor element provides nonvaporized flavor to the user. In most embodiments, the flavor element has an at least some portion coming in contact with the lips and or mouth of the user when providing flavor to the user.

The disclosure includes a flavor element configured for providing flavor to a user of an electronic vaporizer, the flavor element comprises: a flavor material configured to provide the flavor; and an attachment mechanism configured for attachment to the electronic vaporizer. When attached to the electronic vaporizer and during inhalation by the user using the electronic vaporizer, the flavor element is configured to provide the flavor to the user in parallel with an inhalable aerosol provided by the electronic vaporizer, wherein the inhalable aerosol is provided by the electronic vaporizer by at least partially vaporizing a vaporizable substance via a vapor element, wherein the flavor provided via the flavor material is separate from the vaporizable substance. In some embodiments, flavor is provided to the user even if the user is not inhaling from the vaporizer or when the vaporizer is turned off, if the user places his or her lips and or mouth on the flavor material associated with the vaporizer.

In most embodiments, the electronic vaporizer further comprises at least one of a switch, an airflow sensor, a pressure sensor, a controller, a mouthpiece, a pod, a tank, a cartridge, or a combination thereof. For example, the vaporizer may have a shut off switch. For example, the vaporizer is able to detect an inhalation and cause vaporization to occur from or during that inhalation. The vaporizer generally has an outlet end and or a mouthpiece. The vaporizer generally has a source of vaporizable substance that is contained in a pod, tank, or cartridge, or some other container.

In preferred embodiments, the electronic vaporizer has appreciably or essentially no thermal conduction that takes place between the flavor element and the vapor element of the electronic vaporizer.

In some embodiments, the electronic vaporizer is capable of vaporizing and delivering nicotine, a nicotine salt, a nicotine analogue, a nicotine derivative, a nicotine extract, or any combination thereof in a condensation aerosol for inhalation.

In some embodiments, the at least one vaporizable substance includes at least one of tobacco, nicotine, a nicotine salt, a nicotine analogue, a nicotine derivative, a nicotine extract, a nicotine formulation, or any combination thereof.

In some embodiments, the electronic vaporizer is capable of vaporizing and delivering at least one cannabinoid in a condensation aerosol for inhalation.

In some embodiments, the at least one vaporizable substance includes at least one of hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

In some embodiments, the electronic vaporizer is capable of vaporizing and delivering at least one vaporizable substance or formulation that does not contain nicotine or a cannabinoid. In other words, the electronic vaporizer is capable of vaporizing a nicotine-free and or cannabinoid-free substance or formulation, and delivering a nicotine-free and or cannabinoid-free vapor.

In some embodiments, the source of vaporizable substance comprises a liquid-filled pod, tank, or cartridge.

In some embodiments, the source of vaporizable substance comprises a plant material holder, screen, cartridge, or container.

In some embodiments, the source of vaporizable substance comprises a cigarette, a cigarette-like stick (heat stick), or rolled or tubular plug or stick of plant material selected from tobacco leaves, marijuana, or hemp.

Generally, the flavor element is not being vaporized by the vapor element of the electronic vaporizer.

In some embodiments, the flavor element is associated with the housing of the electronic vaporizer.

In some embodiments, the flavor element is associated with the output end of the electronic vaporizer.

In some embodiments, the flavor element is associated with a mouthpiece of the electronic vaporizer.

In some embodiments, the flavor element is associated with a liquid-filled pod, a cartridge, a cigarette, a cigarette-like stick (heat stick), or a rolled or tubular plug or stick of plant material selected from tobacco leaves, marijuana, or hemp.

In some embodiments, the flavor element at least partially comprises a portion or an integral portion of an output end or mouthpiece of the electronic vaporizer.

In some embodiments, the flavor element at least partially comprises an integral component or structural component of the electronic vaporizer.

In some embodiments, the flavor element comprises an attachable and or detachable accessory to the electronic vaporizer body.

In some embodiments, the flavor element comprises an annular ring or sleeve that fits over at least some portion of the electronic vaporizer, mouthpiece, output end, pod, heat stick, or other source of vaporizable substance.

In some embodiments, the flavor element clips on, slides on, adheres to, or attaches to the housing of the electronic vaporizer.

In some embodiments, there is a mechanism for coupling and or uncoupling and or engagement and or disengagement of a flavor element to a vaporizer or vaporizer flavor element receptacle, or of a flavor element vaporizer receptacle to a vaporizer. In some embodiments there is a release mechanism for detaching a flavor element from a vaporizer, directly or indirectly. This release mechanism can comprise a button, switch, or lever. In some embodiments, the release mechanism is under electronic control.

In some embodiments, Velcro is used to removably attach a flavor element to a vaporizer directly or indirectly.

In some embodiments, magnets and or magnetic components and or magnetism removably attaches a flavor element to a vaporizer directly or indirectly.

In some embodiments, the flavor element attaches to the electronic vaporizer and a portion of the flavor element extends proximally toward the output end of the electronic vaporizer.

In some embodiments, the flavor element comprises a tape, film, sticker, or stamp that adheres and or wraps onto at least some portion of the electronic vaporizer, mouthpiece, output end, pod, heat stick, or other source of vaporizable substance.

In some embodiments, the flavor element comprises a port or receptacle for receiving at least some portion of the electronic vaporizer, mouthpiece, output end, pod, heat stick, or other source of vaporizable substance.

In some embodiments, the flavor element comprises a port or receptacle for receiving a candy or flavor insert.

In some embodiments, the flavor element comprises a port or receptacle for receiving a pouch of flavor and or candy.

In some embodiments, the flavor element comprises at least one powder or coating or gel or syrup or paste that at least partially adheres or associates to the output end or a mouthpiece of the electronic vaporizer.

In some embodiments, the flavor element comprises at least one mouthpiece or output end adapter, or mouthpiece or output end extension.

In some embodiments, the flavor element is associated with an at least one external surface of the electronic vaporizer.

In some embodiments, the flavor element is disposable and or for single use.

In some embodiments, the flavor element is refillable, such as refillable with flavor, flavor insert, or candy.

In some embodiments, the flavor element comprises at least one candy.

In some embodiments, the flavor element comprises at least one flavor insert.

In some embodiments, the flavor element comprises at least one flavor in the form of a powder, gel, gelatin, coating, semi-solid, solid, candy cane, licorice, gummy candy, gum, chewing gum, liquid, solution, syrup, paste, hard candy, boiled candy, lollypop, rock candy, or a combination thereof.

In some embodiments, the flavor element provides at least one aroma to be smelled. This may have a synergistic effect with the flavor tasted.

In some embodiments, the flavor element provides at least two flavors or flavor combinations.

In some embodiments, the flavor element comprises at least one of nicotine, caffeine, or cannabinoid, or an analogue or derivative thereof.

In some embodiments, the flavor material includes tobacco, nicotine, a nicotine salt, a nicotine analogue, a nicotine derivative, a nicotine extract, a nicotine formulation, or any combination thereof.

In some embodiments, the flavor material includes hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

In some embodiments, the flavor material includes an at least one substance or formulation that does not contain nicotine or a cannabinoid.

In some embodiments, the flavor element comprises at least one active pharmaceutical ingredient other than nicotine, caffeine, or cannabinoid.

In some embodiments, the flavor element comprises at least one vitamin and or mineral, e.g., vitamin C and or zinc for supplementation.

In some embodiments, the flavor element comprises a plastic embedded or infused with at least one flavor.

In some embodiments, the flavor element is at least partially or fully edible.

In some embodiments, the flavor element comprises natural or artificial sweetener, and or natural or artificial coloring, and or effervescent ingredient.

In some embodiments, the natural sweetener comprises at least one of glucose, dextrose, fructose, *Stevia*. These examples are not meant to be limiting.

In some embodiments, the artificial sweetener comprises at least one of a sugar alcohol, erythritol, xylitol, and sorbitol, and or at least one of sucralose, aspartame, and saccharin. These examples are not meant to be limiting.

Some embodiments of flavor element comprise various numbers of excipient ingredients and/or percent weight/weight of these excipient ingredients. In some embodiments, an at least one flavor element comprises an at least one excipient ingredient selected from the classes of excipients including, but not limited to, antiadherents, binders, coatings, nanoparticles, chelators, buffering agents, acid reacting excipients, alkaline reacting excipients, disintegrants, fillers, diluents, colors/colorants, lubricants, glidants, preservatives, sorbents, salts, flavors, sweeteners, carriers, solvents, surfactants, bioadhesives, mucoadhesives, nanoexcipients/nanoparticles, microencapsulating excipients, chelating excipients, excipients that dissolve over time, biocompatible excipients, non-absorbable excipients, and bioabsorbable excipients and any mixtures and combinations thereof; and can include lipids, liposomes, glycoproteins, proteins, carbohydrates, saccharides, starches, waxes, salts, and polymers. These examples are not meant to be limiting.

In some embodiments, the flavor element comprises honey and or maple syrup.

In some embodiments, the flavor element is inedible or at least partially inedible.

In some embodiments, the flavor element provides at least one flavor selected from tobacco flavor, menthol flavor, non-tobacco flavor, candy flavor, fruit flavor, coffee flavor, chocolate flavor, vanilla flavor, mint flavor, soda flavor, cola flavor, root beer flavor, spirits flavor, wine flavor, whiskey flavor, bourbon flavor, scotch flavor, liquor flavor, beer flavor, vodka flavor, rum flavor, tequila flavor, margarita flavor, daiquiri flavor, colada flavor, or a combination thereof.

In some embodiments, the flavor element comprises at least some ethanol or alcohol and provides at least some ethanol or alcohol content to the user.

In some embodiments, the flavor element comprises at least one anti-addiction or smoking cessation agent or active pharmaceutical ingredient.

The disclosure includes a method of reducing nicotine addiction by reducing the nicotine content of a vaporizable substance in a source of vaporizable substance for an electronic vaporizer in successive manner with subsequent refills of the vaporizable substance and or subsequent replacements of the source of vaporizable substance.

In some embodiments, the method further comprises adding flavor to the vaporizable substance, the flavor selected from tobacco flavor, menthol flavor, non-tobacco flavor, candy flavor, fruit flavor, coffee flavor, chocolate flavor, vanilla flavor, mint flavor, spirits flavor, or a combination thereof.

In some embodiments, the method further comprises adding increasing amounts of flavor to the vaporizable substance.

In some embodiments, the method further comprises adding at least one nonvaporized flavor element to the electronic vaporizer, the at least one nonvaporized flavor element providing a flavor selected from tobacco flavor, menthol flavor, non-tobacco flavor, candy flavor, fruit flavor, coffee flavor, chocolate flavor, vanilla flavor, mint flavor, spirits flavor, or a combination thereof.

In some embodiments, the method further comprises adding increasing amounts of flavor to at least one nonvaporized flavor element associated with the electronic vaporizer.

In some embodiments, the method further comprises adding increasing amounts of nonvaporized flavor elements associated with the electronic vaporizer.

The disclosure includes a method for providing flavor to a user of an electronic vaporizer with a flavor element. This method includes the step of associating the flavor element with the electronic vaporizer. The flavor element is associated with the electronic vaporizer when providing flavor to the user when the user places the electronic vaporizer to the user's lips and or mouth. The electronic vaporizer essentially comprises a housing, an energy source, a source of vaporizable substance, an output end, and a vapor element comprising an electrical resistor or heater. When in use, the electronic vaporizer provides an inhalable aerosol at the output end when the vaporizable substance is at least partially vaporized by the vapor element. The flavor element is noncontacting (does not contact) and unassociated (is not associated) with the vapor element of the electronic vaporizer. The flavor element is separate from the vaporizable substance to be vaporized by the vapor element. The flavor element has an at least some portion coming in contact with the lips and or mouth of the user when providing flavor to the user.

In some embodiments, the method further comprises the step of replenishing a flavor of the flavor element as the flavor is depleted.

In some embodiments, the method further comprises the step of advancing a portion of the flavor element as other portion(s) of the flavor element become depleted. In some embodiments this advancing at least a portion of a flavor element is under electronic control.

In some embodiments, a flavor element contains and/or is capable of holding two or more flavor inserts. For example, the flavor inserts can be candy tablets and the flavor element is capable of dispensing the candy tablets mechanically in a way similar to a PEZ® dispenser.

In some embodiments, the flavor element is a flat area and/or is two-dimensional.

In some embodiments, the flavor element has a volume and/or is three-dimensional.

In some embodiments, the flavor element is ornamental and or consists of a caricature shape and or image; e.g., of a superhero, cartoon character, animal, or famous person. These examples are not meant to be limiting.

In some embodiments, the flavor element is capable of producing light, sounds, and or music, electronically.

In some embodiments, the method further comprises the step of replacing the flavor element when depleted with a fresh or undepleted flavor element.

In some embodiments, the method further comprises the step of replacing the flavor element with a different flavor element having a different flavor.

In some embodiments, the method further comprises the step of adding at least one additional flavor element to create flavor combinations or stronger flavor.

In some embodiments, the method further comprises the step of removing or disassociating the flavor element from the electronic vaporizer when the flavor element is no longer desired.

In some embodiments, the method further comprises the step of retracting at least a portion of the flavor element when the flavor is not desired.

As to the manner of usage and operation of the present disclosure, the same should be apparent from the above description. Accordingly, no further discussion relating to the manner of usage and operation will be provided.

EXAMPLES

Example 1 is a flavor element configured for providing flavor to a user of an electronic vaporizer, the flavor element comprising: a flavor material configured to provide the flavor, wherein the flavor element is configured to attach to the electronic vaporizer, wherein, when attached to the electronic vaporizer and during inhalation by the user using the electronic vaporizer, the flavor element is configured to provide the flavor to the user in parallel with an inhalable aerosol provided by the electronic vaporizer, wherein the inhalable aerosol is provided by the electronic vaporizer by at least partially vaporizing a vaporizable substance via a vapor element, wherein the flavor provided via the flavor material is separate from the vaporizable substance.

In Example 2, the subject matter of Example 1 includes, wherein the flavor element comprises a contact portion that is configured to, when installed on the electronic vaporizer and during inhalation by the user, contact lips or mouth of the user.

In Example 3, the subject matter of Examples 1-2 includes, wherein the flavor element, when installed on the electronic vaporizer and during inhalation by a user, is thermally-isolated from the vapor element of the electronic vaporizer.

In Example 4, the subject matter of Examples 1-3 includes, wherein the vaporizable substance includes tobacco, nicotine, a nicotine salt, a nicotine analogue, a nicotine derivative, a nicotine extract, a nicotine formulation, or any combination thereof.

In Example 5, the subject matter of Examples 1-4 includes, wherein the flavor material includes tobacco, nicotine, a nicotine salt, a nicotine analogue, a nicotine derivative, a nicotine extract, a nicotine formulation, or any combination thereof.

In Example 6, the subject matter of Examples 1-5 includes, wherein the vaporizable substance includes hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

In Example 7, the subject matter of Examples 1-6 includes, wherein the flavor material includes hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

In Example 8, the subject matter of Examples 1-7 includes, wherein the flavor material includes an at least one substance or formulation that does not contain nicotine or a cannabinoid.

In Example 9, the subject matter of Examples 1-8 includes, wherein the flavor element is configured to provide the flavor from the flavor material to the user independent of heat from the vapor element of the electronic vaporizer.

In Example 10, the subject matter of Examples 1-9 includes, wherein the flavor element is configured to attach to a housing of the electronic vaporizer.

In Example 11, the subject matter of Examples 1-10 includes, wherein the flavor element is configured to attach to an output end of the electronic vaporizer.

In Example 12, the subject matter of Examples 1-11 includes, wherein the flavor element is configured to attach to a mouthpiece of the electronic vaporizer.

In Example 13, the subject matter of Examples 1-12 includes, wherein the flavor element is configured to attach to a pod including the vaporizable substance, a cartridge including the vaporizable substance, a cigarette including the vaporizable substance, a cigarette-like stick (heat stick) including the vaporizable substance, or a rolled or tubular plug or stick of the vaporizable substance.

In Example 14, the subject matter of Examples 1-13 includes, wherein the vaporizable substance of the rolled or tubular plug or stick includes a plant material selected from tobacco leaves, marijuana, or hemp.

In Example 15, the subject matter of Examples 1-14 includes, wherein the flavor element is configured to attach to a portion or an integral portion of an output end or mouthpiece of the electronic vaporizer.

In Example 16, the subject matter of Examples 1-15 includes, wherein the flavor element is configured to form an integral component or structural component of the electronic vaporizer when attached to the electronic vaporizer.

In Example 17, the subject matter of Examples 1-16 includes, wherein the flavor element is configured to form an attachable and or detachable accessory to a body of the electronic vaporizer body when attached to the electronic vaporizer.

In Example 18, the subject matter of Examples 1-17 includes, an annular ring or sleeve that fits over a portion of the electronic vaporizer, a mouthpiece, an output end, a heat stick, or a source of the vaporizable substance.

In Example 19, the subject matter of Examples 1-18 includes, wherein the flavor element is configured to clip on, slide on, adhere to, or attach to a portion of a housing of the electronic vaporizer.

In Example 20, the subject matter of Examples 1-19 includes, wherein the flavor element is configured to attach to the electronic vaporizer such that a portion of the flavor element extends proximally toward an output end of the electronic vaporizer.

In Example 21, the subject matter of Examples 1-20 includes, a tape, film, sticker, or stamp that is configured to adhere to a portion of the electronic vaporizer, a mouthpiece, an output end, a pod, a heat stick, or a source of the vaporizable substance.

In Example 22, the subject matter of Examples 1-21 includes, wherein further comprising an at least one mechanical coupling, magnet, Velcro, adhesive, or a combination thereof, configured to attach the flavor element to the electronic vaporizer.

In Example 23, the subject matter of Example 22 includes, wherein the at least one mechanical coupling further includes a release mechanism for uncoupling.

In Example 24, the subject matter of Examples 1-23 includes, wherein the flavor element includes a port or receptacle configured to receive a portion of the electronic vaporizer, a mouthpiece, an output end, a pod, a heat stick, or a source of the vaporizable substance.

In Example 25, the subject matter of Examples 1-24 includes, a port or receptacle for receiving an insert that includes the flavor material.

In Example 26, the subject matter of Examples 1-25 includes, a port or receptacle for receiving a pouch that includes the flavor material.

In Example 27, the subject matter of Examples 1-26 includes, wherein the flavor material at least partially attaches to an output end or a mouthpiece of the electronic vaporizer.

In Example 28, the subject matter of Example 27 includes, wherein the flavor material comprises at least one of a powder, a coating, a gel, a syrup, a paste, a sheet, or any combination thereof configured to adhere to the output end or the mouthpiece of the electronic vaporizer.

In Example 29, the subject matter of Examples 1-28 includes, a mouthpiece adapter, an output end adapter, a mouthpiece extension, an output end extension, or any combination thereof.

In Example 30, the subject matter of Examples 1-29 includes, wherein the flavor element is a single-use device.

In Example 31, the subject matter of Examples 1-30 includes, wherein the flavor element is a refillable device.

In Example 32, the subject matter of Examples 1-31 includes, wherein the flavor material includes a candy.

In Example 33, the subject matter of Examples 1-32 includes, an insert that includes the flavor material.

In Example 34, the subject matter of Examples 1-33 includes, wherein the flavor material includes powder, gel, gelatin, coating, semi-solid, solid, candy cane, licorice, gummy candy, gum, liquid, solution, syrup, paste, hard candy, boiled candy, lollypop, rock candy, or any combination thereof.

In Example 35, the subject matter of Examples 1-34 includes, wherein the flavor material further includes an aroma.

In Example 36, the subject matter of Examples 1-35 includes, wherein the flavor material further includes at least two flavors or flavor combinations.

In Example 37, the subject matter of Examples 1-36 includes, wherein the flavor element is at least partially edible.

In Example 38, the subject matter of Examples 1-37 includes, wherein the flavor material comprising a natural or artificial sweetener, natural or artificial coloring, an effervescent ingredient, or any combination thereof.

In Example 39, the subject matter of Examples 1-38 includes, wherein the flavor material includes a tobacco flavor, a menthol flavor, a non-tobacco flavor, a candy flavor, a fruit flavor, a coffee flavor, a chocolate flavor, a vanilla flavor, a mint flavor, a soda flavor, a cola flavor, a root beer flavor, a spirits flavor, a wine flavor, a whiskey flavor, a bourbon flavor, a scotch flavor, a liquor flavor, a beer flavor, a vodka flavor, a rum flavor, a tequila flavor, a margarita flavor, a daiquiri flavor, a colada flavor, or any combination thereof.

In Example 40, the subject matter of Examples 1-39 includes, wherein the flavor material includes an ethanol or alcohol.

In Example 41, the subject matter of Examples 1-40 includes, wherein the flavor material includes an anti-addiction, smoking cessation agent, an active pharmaceutical ingredient, a vitamin, a mineral, or any combination thereof.

In Example 42, the subject matter of Examples 1-41 includes, wherein the flavor material is further integrated, embedded, or infused in a structure or material of the electronic vaporizer, or a mouthpiece, cartridge, heat stick, or pod of the electronic vaporizer.

Example 43 is a method, comprising: providing a first vaporizable substance having a first nicotine content for use in an electronic vaporizer; and in response to the first vaporizable substance being consumed, providing a second vaporizable substance having a second nicotine content for use in the electronic vaporizer, wherein the first nicotine content is higher than the second nicotine content.

In Example 44, the subject matter of Example 43 includes, adding a predetermined amount of flavor material to the second vaporizable substance to mask a reduction from the first nicotine content to the second nicotine content.

In Example 45, the subject matter of Examples 43-44 includes, wherein the flavor material includes tobacco flavor, menthol flavor, non-tobacco flavor, candy flavor, fruit flavor, coffee flavor, chocolate flavor, vanilla flavor, mint flavor, spirits flavor, or a combination thereof.

In Example 46, the subject matter of Examples 44-45 includes, in response to the second vaporizable substance being consumed, providing a third vaporizable substance having a third nicotine content for use in the electronic vaporizer, wherein the second nicotine content is higher than the third nicotine content.

In Example 47, the subject matter of Example 46 includes, adding a second predetermined amount of the flavor material to the third vaporizable substance to mask a reduction from the second nicotine content to the third nicotine content, wherein the second predetermined amount is greater than the predetermined amount.

In Example 48, the subject matter of Examples 43-47 includes, adding a nonvaporized flavor element to the electronic vaporizer for use with the first vaporizable substance, the nonvaporized flavor element including a first amount of the flavor material configured to provide a flavor to a user using the electronic vaporizer.

In Example 49, the subject matter of Example 48 includes, wherein the flavor includes tobacco flavor, menthol flavor, non-tobacco flavor, candy flavor, fruit flavor, coffee flavor, chocolate flavor, vanilla flavor, mint flavor, spirits flavor, or a combination thereof.

In Example 50, the subject matter of Examples 48-49 includes, adding a second amount of the flavor material to the nonvaporized flavor element for use with the second vaporizable substance, wherein the second amount of the flavor material is greater than the first amount.

In Example 51, the subject matter of Examples 48-50 includes, adding a second nonvaporized flavor element to the electronic vaporizer for use with the second vaporizable substance in parallel with the nonvaporized flavor element, the second nonvaporized flavor element including the first amount of the flavor material configured to provide additional flavor to a user using the electronic vaporizer that is greater than the first flavor amount.

In Example 52, the subject matter of Examples 43-51 includes, in response to the second vaporizable substance being consumed, providing a third vaporizable substance that is nicotine content free for use in the electronic vaporizer.

Example 53 is a method for providing flavor to a user of an electronic vaporizer with a flavor element, the method comprising, during inhalation by the user using the electronic vaporizer: providing flavor from a flavor material of a flavor element attached to the electronic vaporizer in parallel with an inhalable aerosol provided by the electronic vaporizer, wherein the inhalable aerosol is provided by the electronic vaporizer by at least partially vaporizing a vaporizable substance via a vapor element, wherein the flavor element is separate from the vaporizable substance.

In Example 54, the subject matter of Example 53 includes, replacing the flavor material of the flavor element with new flavor material in response to the flavor material being consumed below a threshold level.

In Example 55, the subject matter of Examples 53-54 includes, advancing a portion of the flavor element in response to the flavor material being consumed below a threshold level.

In Example 56, the subject matter of Examples 53-55 includes, replacing the flavor element with a new flavor element in response to the flavor material being consumed below a threshold level.

In Example 57, the subject matter of Examples 53-56 includes, replacing said flavor element with a different flavor element having a different flavor.

In Example 58, the subject matter of Examples 53-57 includes, adding at least one additional flavor element to the electronic vaporizer.

In Example 59, the subject matter of Examples 53-58 includes, removing the flavor element from the electronic vaporizer.

In Example 60, the subject matter of Examples 53-59 includes, retracting at least a portion of the flavor element such that provision of the flavor ceases during inhalation by the user using the electronic vaporizer.

In Example 61, the subject matter of Examples 53-60 includes, replacing the flavor material of the flavor element with a different flavor material to change flavors.

Example 62 is at least one machine-readable medium including instructions that, when executed by processing circuitry, cause the processing circuitry to perform operations to implement of any of Examples 1-61.

Example 63 is an apparatus comprising means to implement of any of Examples 1-61.

Example 64 is a system to implement of any of Examples 1-61.

Example 63 is a method to implement of any of Examples 1-42.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

Other embodiments of the disclosure will be apparent to those skilled in the art from consideration of the specification and practice of the disclosure disclosed herein. It is intended that the specification and examples be considered as exemplary only, with a true scope and spirits of the disclosure being indicated by the following claims.

What is claimed is:

1. A flavor element for a rolled heat stick warmer system comprising a rolled heat stick warmer having an at least one heating element and a rolled heat stick; said flavor element comprising:
   a contact portion including a flavor material configured to provide nonvaporized flavor, wherein the contact portion is configured to contact a mouth of a user when the rolled heat stick of the rolled heat stick warmer system is placed in the mouth of the user; and
   a structure that is configured to attach the contact portion of the flavor element to an exterior of the rolled heat stick warmer system;
   wherein, when attached to the rolled heat stick warmer system and during inhalation by the user using the rolled heat stick warmer system, the flavor element is configured to provide the nonvaporized flavor to the user in parallel with an inhalable aerosol provided by the rolled heat stick warmer system, wherein the inhalable aerosol is provided by the rolled heat stick warmer system by at least partially heating a plant material or plant-derived substance of the rolled heat stick by the at least one heating element;
   wherein the nonvaporized flavor provided by the flavor material is separate from the plant material or plant-derived substance of the rolled heat stick.

2. The flavor element of claim 1, wherein the structure is configured to enable removal of the contact portion of the flavor element or the flavor element from the rolled heat stick warmer system, and optionally including for replacement.

3. The flavor element of claim 1, wherein the flavor element, when installed on the rolled heat stick warmer system and during inhalation by a user, is thermally-isolated from the heating element of the rolled heat stick warmer system.

4. The flavor element of claim 1, wherein the plant material or plant-derived substance of the rolled heat stick includes tobacco leaves, tobacco leaf extract, tobacco oils, nicotine, a nicotine salt, a nicotine analogue, a nicotine derivative, a nicotine extract, a formulation including tobacco leaf or tobacco leaf extract, a nicotine formulation, or any combination thereof.

5. The flavor element of claim 1, wherein the flavor material includes tobacco, nicotine, a nicotine salt, a nicotine analogue, a nicotine derivative, a nicotine extract, a nicotine formulation, or any combination thereof.

6. The flavor element of claim 1, wherein the plant material or plant-derived substance of the rolled heat stick includes *cannabis, cannabis* oils, *cannabis* flower, *cannabis* leaves, hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

7. The flavor element of claim 1, wherein the flavor material includes *cannabis*, hemp, marijuana, a cannabinoid, cannabidiol, tetrahydrocannabinol, a tetrahydrocannabinol salt, a tetrahydrocannabinol analogue, a tetrahydrocannabinol derivative, a tetrahydrocannabinol extract, a cannabinoid formulation, or any combination thereof.

8. The flavor element of claim 1, wherein the flavor material includes an at least one substance or formulation that does not contain nicotine or a cannabinoid.

9. The flavor element of claim 1, wherein the flavor element is configured to provide the nonvaporized flavor from the flavor material to the user independent of heat from the heating element of the rolled heat stick warmer system, and further can provide nonvaporized flavor when the rolled heat stick warmer system is turned off or when the user is not inhaling from the rolled heat stick.

10. The flavor element of claim 1, wherein the flavor element is configured to attach to a housing of the rolled heat stick warmer, an output end of the rolled heat stick warmer system, a mouthpiece or optional mouthpiece of the rolled heat stick warmer system, a rolled heat stick of the rolled heat stick warmer system, or a combination thereof.

11. The flavor element of claim 1, wherein said rolled heat stick further comprising a wrapper structure; said wrapper structure at least partially surrounding an aerosolizable plant material or plant-derived substance that is in a form of a plug or tubular roll; said wrapper structure comprised of paper, film, polymer, plastic, foil, or a combination thereof; said rolled heat stick further optionally comprising an at least one filter.

12. The flavor element of claim 1, wherein the rolled heat stick contains a plant material or plant extract from a plant other than, or in addition to, a tobacco or *cannabis* plant.

13. The flavor element of claim 1, wherein the rolled heat stick contains a vaporizable substance in addition to plant material or plant-derived substance.

14. The flavor element of claim 1, wherein the flavor element is or is configured to form an integral component or structural component of the rolled heat stick or rolled heat stick warmer.

15. The flavor element of claim 1, wherein the flavor element is configured to form a detachable accessory to the rolled heat stick warmer system.

16. The flavor element of claim 1, wherein the flavor element is configured to clip on, slide on, adhere to, fit over or in, or attach to a portion of the rolled heat stick warmer system.

17. The flavor element of claim 1, wherein the flavor element is configured to attach to the rolled heat stick warmer system such that a portion of the flavor element extends proximally toward or past an output end of the rolled heat stick warmer system.

18. The flavor element of claim 1, further comprising a tape, film, sticker, or stamp that is configured to adhere to a portion of the rolled heat stick warmer system, a rolled heat stick warmer, a mouthpiece, an output end, or a rolled heat stick.

19. The flavor element of claim 1, wherein further comprising an at least one mechanical coupling, magnet, a hook and loop fastener, adhesive, or a combination thereof, configured to attach the flavor element to the rolled heat stick warmer system, and further optionally comprising a release mechanism for uncoupling.

20. The flavor element of claim 1, wherein the flavor material at least partially attaches to an output end or a mouthpiece or rolled heat stick of the rolled heat stick warmer system.

21. The flavor element of claim 1, wherein the flavor element is a single-use device.

22. The flavor element of claim 1, wherein the flavor element is a refillable device.

23. The flavor element of claim 1, wherein the flavor material includes a candy.

24. The flavor element of claim 1, further comprising and receiving an insert that includes the flavor material, said insert further optionally removable.

25. The flavor element of claim 1, wherein the flavor material includes at least one of a powder, gel, gelatin, coating, semi-solid, solid, candy cane, licorice, gummy candy, gum, liquid, solution, syrup, paste, sheet, hard candy, boiled candy, lollypop, rock candy, or any combination thereof.

26. The flavor element of claim 1, wherein the flavor material further includes an aroma.

27. The flavor element of claim 1, wherein the flavor material further includes at least two flavors or flavor combinations.

28. The flavor element of claim 1, wherein the flavor element is at least partially edible.

29. The flavor element of claim 1, wherein the flavor material further comprising a natural or artificial sweetener, natural or artificial coloring, an effervescent ingredient, or any combination thereof.

30. The flavor element of claim 1, wherein the flavor material includes a tobacco flavor, a *cannabis* flavor, a menthol flavor, a non-tobacco flavor, a sweet flavor, a candy flavor, a fruit flavor, a coffee flavor, a chocolate flavor, a vanilla flavor, a mint flavor, a soda flavor, a cola flavor, a root beer flavor, a spirits flavor, a wine flavor, a whiskey flavor, a bourbon flavor, a scotch flavor, a liquor flavor, a beer flavor, a vodka flavor, a rum flavor, a tequila flavor, a margarita flavor, a daiquiri flavor, a colada flavor, or any combination thereof.

31. The flavor element of claim 1, wherein the flavor material includes an ethanol or alcohol.

32. The flavor element of claim 1, wherein the flavor material includes an anti-addiction, smoking cessation agent, an active pharmaceutical ingredient, a vitamin, a mineral, or any combination thereof.

33. The flavor element of claim 1, wherein the flavor material is further integrated, embedded, or infused in a structure or material of the rolled heat stick warmer system, or a mouthpiece, cartridge, filter, or rolled heat stick of the rolled heat stick warmer system.

34. The flavor element of claim 1, wherein an artificial plant material, synthetic chemical or material, lab created material, biotech grown or derived material from or including algae, yeast, or other microorganism, or any combination thereof of the rolled heat stick, is used instead of or in combination with said plant material or plant-derived substance.

35. A flavor element for a rolled heat stick warmer system comprising a rolled heat stick warmer having an at least one heating element and a rolled heat stick; the flavor element comprising:
a contact portion including a flavor material configured to provide a nonvaporized flavor, wherein the contact portion is configured to contact a mouth of a user; and
a structure that is configured to attach the contact portion of the flavor element to an exterior of the rolled heat stick warmer system;
wherein, when attached to the rolled heat stick warmer system, the flavor element is configured to provide the nonvaporized flavor to the user when in contact with the mouth of the user when an inhalable aerosol is not provided by the rolled heat stick warmer system by at least partially heating a plant material or plant-derived substance of the rolled heat stick by the at least one heating element, including when the user is not inhaling from the rolled heat stick;
wherein the nonvaporized flavor provided by the flavor material is separate from the plant material or plant-derived substance contained inside the rolled heat stick.

* * * * *